(12) United States Patent
Scott et al.

(10) Patent No.: US 12,329,561 B2
(45) Date of Patent: **\*Jun. 17, 2025**

(54) X-RAY IMAGING SYSTEM

(71) Applicant: Ibex Innovations Limited, Sedgefield (GB)

(72) Inventors: Paul Scott, Sedgefield (GB); Neil Loxley, Sedgefield (GB); Adam Ratcliffe, Sedgefield (GB)

(73) Assignee: Ibex Innovations Limited, Durham (GB)

( \* ) Notice: Subject to any disclaimer, the term of this patent is extended or adjusted under 35 U.S.C. 154(b) by 0 days.

This patent is subject to a terminal disclaimer.

(21) Appl. No.: 18/635,414

(22) Filed: Apr. 15, 2024

(65) Prior Publication Data

US 2024/0268779 A1 Aug. 15, 2024

Related U.S. Application Data

(63) Continuation of application No. 17/271,722, filed as application No. PCT/GB2019/052439 on Aug. 30, 2019, now Pat. No. 11,992,356.

(30) Foreign Application Priority Data

Aug. 31, 2018 (GB) ...................... 1814238

(51) Int. Cl.
*G06T 7/70* (2017.01)
*A61B 6/00* (2006.01)
(Continued)

(52) U.S. Cl.
CPC .......... *A61B 6/5282* (2013.01); *G06T 3/4007* (2013.01); *G06T 5/70* (2024.01);
(Continued)

(58) Field of Classification Search
CPC ..... A61B 6/5282; A61B 6/505; A61B 6/5217; A61B 6/027; A61B 6/582; A61B 6/5211;
(Continued)

(56) References Cited

U.S. PATENT DOCUMENTS

| 4,413,353 A | 11/1983 | Macovski et al. |
| 5,440,647 A | 8/1995 | Floyd et al. |

(Continued)

FOREIGN PATENT DOCUMENTS

| CN | 101109718 | 1/2008 |
| CN | 101472524 | 7/2009 |

(Continued)

OTHER PUBLICATIONS

International Search Report and Written Opinion issued by the International Searching Authority (ISA/EP) in PCT Application No. PCT/GB2019/052439 on Oct. 23, 2019, 16 pages.

(Continued)

*Primary Examiner* — Jose L Couso
(74) *Attorney, Agent, or Firm* — Meunier Carlin & Curfman LLC

(57) ABSTRACT

A method of performing scatter correction on an X-ray image is disclosed. The method comprises obtaining an input image for processing based on a source X-ray image of a sample acquired using an X-ray detector, and determining a model of the sample based on the input image. The model is then evaluated by computing, based on the model, simulated X-ray image data and evaluating the simulated image data against the input image to determine whether a convergence criterion is fulfilled. An updated model of the sample is generated if the convergence criterion is not fulfilled. The model evaluating step is repeated based on one or more successive updated models until the convergence criterion is fulfilled in a final iteration, and scatter correction (Continued)

Figure 1:
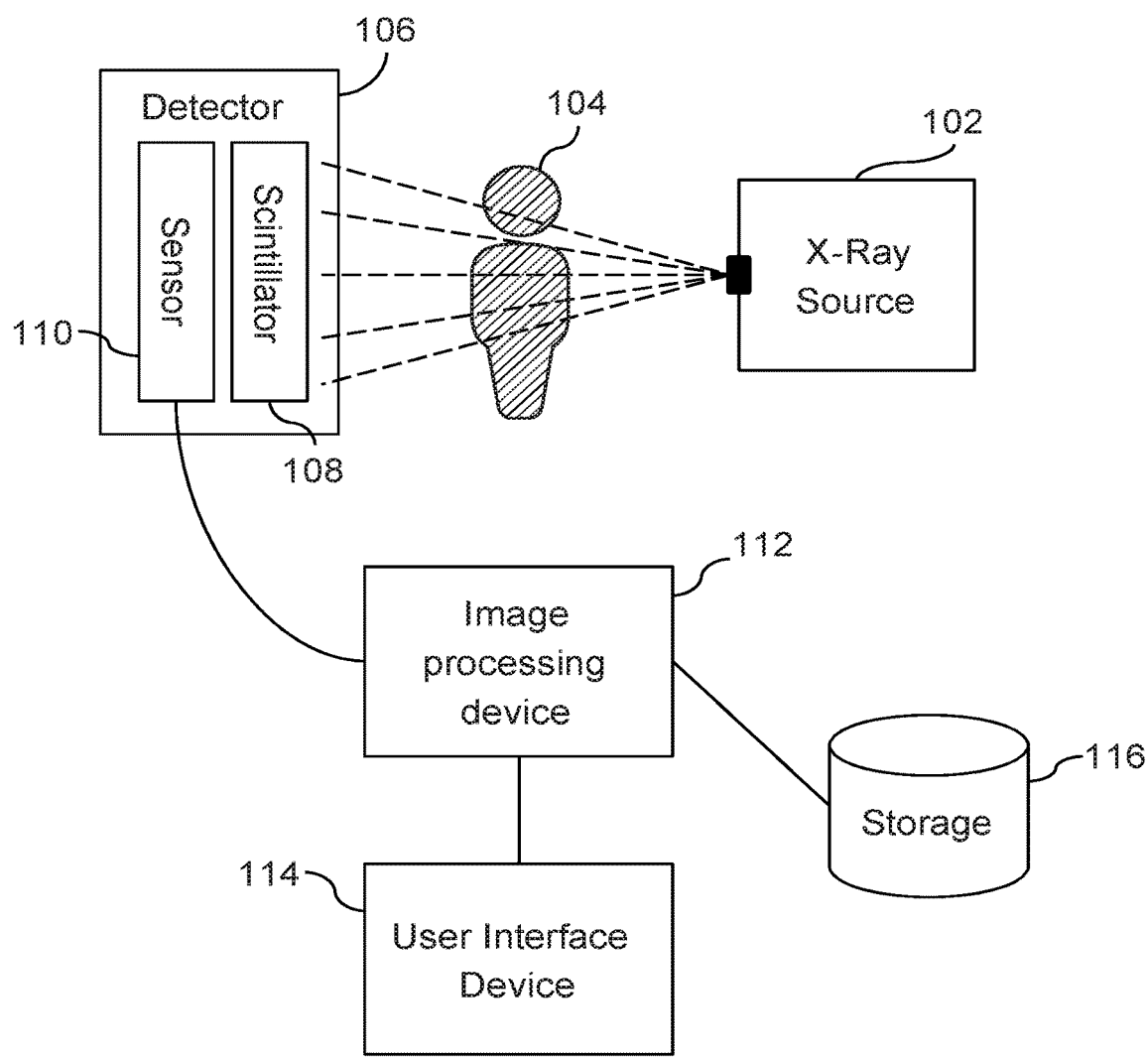

is then performed on the source X-ray image using simulated image data computed during the final iteration.

20 Claims, 10 Drawing Sheets

(51) Int. Cl.
  *G06T 3/4007* (2024.01)
  *G06T 5/70* (2024.01)
  *G06T 7/00* (2017.01)
(52) U.S. Cl.
  CPC .. *G06T 7/0014* (2013.01); *G06T 2207/10116* (2013.01); *G06T 2207/20224* (2013.01); *G06T 2207/30004* (2013.01)
(58) Field of Classification Search
  CPC ....... A61B 6/5294; A61B 6/03; G06T 3/4007; G06T 5/70; G06T 7/0014; G06T 2207/10116; G06T 2207/20224; G06T 2207/30004; G06T 5/73; G06T 5/00; G06T 7/0012; G06T 5/002; G06T 5/003; G06T 7/007; G06T 7/60; G06T 11/008; G06T 19/006; G06T 2207/20182; Y10S 378/901; G16H 30/20; G16H 30/40
  See application file for complete search history.

(56) References Cited

U.S. PATENT DOCUMENTS

| | | | |
|---|---|---|---|
| 5,878,108 A | 3/1999 | Baba et al. | |
| 7,308,072 B2 | 12/2007 | Rührnschopf | |
| 7,551,716 B2 | 6/2009 | Rührnschopf | |
| 8,326,011 B2 | 12/2012 | Star-Lack et al. | |
| 9,633,480 B2 | 4/2017 | Enomoto et al. | |
| 10,588,592 B2 | 3/2020 | Scott et al. | |
| 10,631,815 B2 | 4/2020 | Rui et al. | |
| 11,992,356 B2 * | 5/2024 | Scott | G06T 3/4007 |
| 2005/0074097 A1 | 4/2005 | Ulyanenkov | |
| 2005/0111626 A1 | 5/2005 | Xu et al. | |
| 2005/0190888 A1 | 9/2005 | Schmitt | |
| 2006/0008046 A1 | 1/2006 | Ruhrnschopf | |
| 2008/0013673 A1 | 1/2008 | Ruhmschopf et al. | |
| 2008/0095313 A1 | 4/2008 | Ruhrnschopf et al. | |
| 2009/0086907 A1 | 4/2009 | Smith | |
| 2009/0290682 A1 | 11/2009 | Star-Lack et al. | |
| 2010/0046696 A1 | 2/2010 | Maltz | |
| 2011/0311032 A1 | 12/2011 | Miller | |
| 2012/0148156 A1 | 6/2012 | Sehnert | |
| 2013/0044860 A1 | 2/2013 | Nicholson et al. | |
| 2013/0259344 A1 | 10/2013 | Petersilka et al. | |
| 2014/0222385 A1 | 8/2014 | Muenster et al. | |
| 2015/0342554 A1 | 12/2015 | Mentrup et al. | |
| 2015/0371414 A1 | 12/2015 | Choi et al. | |
| 2016/0086328 A1 | 3/2016 | Enomoto et al. | |
| 2016/0140720 A1 | 5/2016 | Naito | |
| 2017/0238894 A1 | 8/2017 | Scott et al. | |
| 2017/0273649 A1 | 9/2017 | Tajima | |
| 2017/0360391 A1 | 12/2017 | Kawamura | |
| 2018/0014806 A1 | 1/2018 | Lu et al. | |
| 2018/0146935 A1 | 5/2018 | Song et al. | |
| 2019/0197740 A1 | 6/2019 | Lu et al. | |

FOREIGN PATENT DOCUMENTS

| | | |
|---|---|---|
| CN | 103284734 | 9/2013 |
| EP | 0223305 | 5/1987 |
| GB | 2547775 | 8/2017 |
| GB | 2563115 | 12/2018 |
| JP | 06-014911 | 1/1985 |
| JP | S63-082627 | 4/1988 |
| JP | 05-303154 | 11/1993 |
| JP | H10-314152 | 12/1998 |
| JP | 2003175026 | 6/2003 |
| JP | 2008-502395 | 1/2008 |
| JP | 2009-018110 | 1/2009 |
| JP | 2015043959 | 3/2015 |
| JP | 2015181649 | 10/2015 |
| SU | 962797 | 9/1982 |
| WO | 1997/030459 | 8/1997 |
| WO | 2006/082557 | 8/2006 |
| WO | 2009/004523 | 1/2009 |
| WO | 2009136400 | 11/2009 |
| WO | 2009141767 | 11/2009 |
| WO | 2011/027390 | 3/2011 |
| WO | 2011/058612 | 5/2011 |
| WO | 2016051212 | 4/2016 |
| WO | 2018/158577 | 9/2018 |

OTHER PUBLICATIONS

Search Report issue by the Intellectual Property Office of the United Kingdom in Application No. GB1814238.0 on Feb. 28, 2019, 6 pages.

Search Report issue by the Intellectual Property Office of the United Kingdom in Application No. GB1814238.0 on Oct. 10, 2019, 3 pages.

Search Report issued for Application No. GB2210634.8, dated Nov. 10, 2022.

Japanese Notification of Reason for Refusal, Application No. 2021-536421, dated May 23, 2023.

Ibex Innovations Ltd. "White Paper: Gridless imaging from any digital radiography system." Downloaded from https://www.ibexinnovations.co.uk/.2017. 8 pages.

Medical Physics, vol. 38 (2011), Ruhrnschopf & Klingenbeck, "A general framework and review of scatter correction methods in cone beam CT. Part 2: Scatter estimation approaches", pp. 5186-5199.

Medical Physics, vol. 38 (2011), Sun et al. "Correction for patient-table induced scattered radiation in cone-beam computed tomography (CBCT)", pp. 2058-2073.

IEEE Transactions on Nuclear Science, vol. 53 (2006), Ahn et al. "A scatter correction using thickness iteration in dual-energy radiography", pp. 133-138.

* cited by examiner

X-RAY IMAGING SYSTEM

This application is continuation of U.S. patent application Ser. No. 17/271,722 filed Feb. 26, 2021, which is a national stage application filed under 35 U.S.C. § 371 of PCT/GB2019/052439 filed Aug. 30, 2019, which claims priority to and benefit of GB patent application serial number 1814238.0 filed Aug. 31, 2018, which are fully incorporated by reference and made a part hereof.

The present invention relates to systems and methods for processing x-ray images to perform scatter correction. Described systems may also produce a tissue model of imaged tissue which allows bone density distributions to be inferred.

Some known x-ray imaging systems (e.g. DXA dual energy scan systems) employ two distinct x-ray energy levels and can infer bone mineral density by determining the mass attenuation coefficient at the different energy levels. However, the dual energy requirement significantly increases cost and complexity of the imaging equipment. Another approach uses a multi-absorption plate (MAP) placed in the path of the beam, as described in GB2498615 (the entire contents of which are herein incorporated by reference). The MAP applies variable perturbation to the energy spectrum of the x-ray beam across the image in such a way that material properties can be identified. However, use of the MAP requires the addition of a physical component to the imaging system.

The quality of images acquired by x-ray imaging systems is usually negatively affected by scatter. Ideally, an x-ray image would be based only on the partial absorption of x-rays passing through the subject in a straight line ("direct beam"), allowing inferences regarding the material (e.g. bone density) in the path of the beam. However, in addition to partial absorption, some x-ray photons are scattered by the material, and these scattered photons can contribute noise to the final image. One approach to addressing this problem is the use of an anti-scatter grid placed between the x-ray detector and the subject. An anti-scatter grid absorbs a large proportion of scattered radiation whilst allowing most direct radiation to pass through to the x-ray detector. However, some of the direct radiation may be still be absorbed by the anti-scatter grid, and this increased absorption typically necessitates increasing the x-ray dosage to which the subject being imaged is exposed. This is often undesirable, especially in medical imaging applications.

Anti-scatter grids also frequently introduce undesirable image artefacts into the final image and are often difficult to use due to geometrical constraints, particularly in portable systems.

A previous approach to scatter correction based on use of a MAP is described in WO 2016/051212 (the entire contents of which are incorporated herein by reference).

The present invention seeks to alleviate some of the problems inherent in use of a MAP or anti-scatter grid.

Accordingly, in a first aspect of the invention, there is provided a method of performing scatter correction on an X-ray image, comprising: obtaining an input image for processing based on a source X-ray image of a sample acquired using an X-ray detector; and determining a model of the sample based on the input image. The method comprises evaluating the model by a process comprising: computing, based on the model, simulated X-ray image data; evaluating the simulated image data against the input image to determine whether a convergence criterion is fulfilled; and generating an updated model of the sample if the convergence criterion is not fulfilled. The method further comprises repeating the model evaluating process based on one or more successive updated models until the convergence criterion is fulfilled in a final iteration; and performing scatter correction on the source X-ray image using simulated image data computed during the final iteration.

By producing a model of the sample based on the original image and then iteratively refining the model in the described manner, it is possible to obtain simulated image data that matches real X-ray images sufficiently closely to be used for scatter correction, without the need for a MAP or anti-scatter grid.

The model preferably comprises, for each of a plurality of locations, each location preferably corresponding to at least one pixel of the input image and/or at least one volume element in the sample, one or both of: a thickness value indicating a thickness of the sample at the location; and a material value indicative of a material composition of the sample at the location; preferably wherein the sample is modelled as consisting of (at least) first and second material types (possibly more than two material types may be used), the material value indicating material composition in relation to (at least) the first and second material types, preferably by indicating a proportion (or other relative quantity) of one of the first and second material types at the location (e.g. relative to the whole volume element as a material fraction, or relative to the other material type as a material ratio), or by otherwise indicating an amount or proportion of one or more material types at the location.

The simulated image data preferably comprises: a direct beam image (also referred to herein as a direct beam estimate) indicating an estimated contribution to the input image from X-ray photons passing through the sample without being scattered, and a scatter image (also referred to herein as a scatter estimate) indicating an estimated contribution to the input image from X-ray photons scattered by the sample.

Preferably, computing simulated image data comprises computing simulated direct beam image data at each image location of the input image based on material composition and thickness values specified for the location in the model, and computing simulated scatter image data at each image location based on material composition and thickness values specified in the model for a plurality of other image locations.

Preferably, computing simulated image data comprises determining a plurality of scatter kernels, each preferably specifying a scatter contribution due to the sample material at a first location to image pixels at one or more further locations, and generating a scatter image based on combining (e.g. summing or convolving) the plurality of scatter kernels, wherein the scatter kernels are optionally derived from a scatter kernel database based on the model, preferably by retrieving one or more precomputed scatter kernels and/or interpolating precomputed scatter kernels. The method may comprise modifying (the shape of) scatter kernels according to the material composition specified by the model for volume elements along scattered ray paths (e.g. paths from the first location to the one or more further locations). In other words, the contribution to target pixels due to a given volume element may be determined from the scatter kernel for the volume element (e.g. identified from thickness and composition values), as modified based on modelled material compositions of volume elements along paths to the target pixels.

The scatter correction is preferably performed based on the scatter image (preferably as determined during the final iteration), preferably by subtracting an image correction determined based on the scatter image from the source X-ray image, optionally wherein the input image is obtained by downscaling the source X-ray image, the image correction determined by upscaling the scatter image to the resolution of the source X-ray image.

Evaluating the simulated image data against the input image preferably comprises applying a transfer function to one of the simulated image data and the input image and performing the evaluation after application of the transfer function, preferably wherein the transfer function defines a translation between simulated X-ray data and X-ray data obtained using the detector to make simulated X-ray data comparable to X-ray data obtained using the detector. The transfer function may define a respective translation for each pixel location of the input image and simulated X-ray data, for translating intensity values between simulated and real image domains, the translation optionally in the form of a polynomial function, preferably of at least second degree, or other mathematical function. The transfer function may be empirically determined, preferably based on analysing a set of X-ray images acquired for predetermined known material samples and a set of corresponding simulated images generated for the known samples by the simulator.

Preferably, evaluating the simulated image data against the input image comprises computing an error image based on the simulated image data and the input image, optionally by subtracting the scatter image and the direct beam image from the input image (which encompasses subtracting them individually or subtracting their sum), optionally wherein the error image comprises a plurality of error values for respective pixels based on the subtracting. Evaluating the simulated image data preferably further comprises computing an error measure (preferably as a single numerical value) based on the error image, the error measure preferably indicating a degree of divergence or difference of the error image from a zero image. The error measure may be computed based on a sum of error values specified by individual pixels of the error image.

Evaluating the simulated image data may further comprise comparing the error measure to a threshold, the convergence criterion preferably based on the threshold, the method preferably comprising determining that the convergence criterion is met if the error measure falls below the threshold.

Preferably, determining a model of the sample based on the input image comprises analysing the input image to classify one or more pixels as corresponding to a known material composition, preferably based on pixel intensity and/or feature detection, and determining the model using the classified pixels, optionally wherein the known material composition corresponds to the sample consisting of a single material at the pixel location (e.g. a material fraction of 1).

Generating an updated model of the sample preferably comprises performing scatter correction on the input image based on the simulated image data (preferably by subtracting a scatter image of the simulated image data from the input image), and generating the updated model based on the scatter-corrected input image. In this way, simulated image data, in particular a scatter estimate determined during a given iteration of the process, can be used as the basis for a preliminary scatter-corrected image which in turn can be used to produce an improved model, which can then produce improved simulated image data during a subsequent iteration. This approach can enable iterative refinement of the model and scatter estimate to thereby improve accuracy of the final scatter correction.

The method may comprise performing a model generation process for an image comprising: obtaining a classification of one or more pixels of the image as corresponding to a given material composition, the classification optionally based on comparison of intensity value(s) of the pixels to a threshold; determining an estimated material thickness value for each of the one or more classified pixels, optionally based on data defining expected thickness values for pixels having the given material composition or defining non-implausible sets of thickness and material composition values for given intensity values; fitting a thickness function to the image based on estimated thickness values for the classified pixels, the thickness function indicating an estimated material thickness for each pixel of the image; estimating material composition values for each pixel based on the estimated material thickness values specified by the thickness function, optionally by determining for each pixel a set of non-implausible material composition values based on the material thickness value for the pixel and deriving the material composition value for the pixel from the set of non-implausible material values, optionally by averaging the set of non-implausible material values; and determining a model comprising for each pixel a material composition value and a thickness value based on the estimated material composition values and the estimated material thickness values.

The above process may be used for the initial model generation and/or for generation of updated models during iterations of the refinement loop. Thus the method may include performing the step of determining a model of the sample based on the input image by applying the above model generation process to the input image and/or may include performing the step of generating an updated model of the sample by computing a scatter-corrected version of the input image using the simulated image data (preferably by removing a simulated scatter image from the input image), and applying the model generation process to the scatter-corrected input image.

The method may comprise, after generating the updated model of the sample, computing new simulated image data based on the updated model and evaluating the new simulated image data against the simulated image data computed based on the (previous) model, and selecting the updated model for use in the subsequent iteration of the model evaluation process if the new simulated image data represents a simulated X-ray image closer to the input image than the (previous) simulated image data (e.g. in terms of having a lower error measure). On the other hand, if the (previous) simulated image data represents a simulated X-ray image closer to the input image than the new simulated image data (e.g. having a lower error measure), the method may include computing a revised updated model based on (optionally by averaging) the updated model and a selected model determined in a previous iteration, and selecting the revised updated model for use in the subsequent iteration. The selected previous model may be a better or best previous model, e.g. a model producing a lower (preferably lowest) magnitude error measure (preferably of opposite sign) when evaluating simulated image data against the input image.

The input image may be the source X-ray image or a pre-processed, preferably downsampled version of the source X-ray image. The simulated image data is preferably generated at the resolution of the input image. The model is preferably at that same resolution, preferably specifying respective material and/or thickness values for each pixel location of the input image/simulated image data.

The method may comprise outputting one or more of: the scatter-corrected source X-ray image; and model data, preferably thickness and/or material composition data, for the sample, preferably based on the model of the sample used to generate the simulated image data determined to meet the convergence criterion during the final iteration. The model data may be an upscaled/higher-resolution version of the final iteration model. The method may comprise deriving and outputting density information, e.g. bone density information, based on the model.

The sample may comprises biological tissue and/or the model may comprise a tissue model, optionally wherein the tissue model defines the sample as a plurality of thickness values and a plurality of composition values for respective volume elements in the tissue sample, preferably wherein the composition values specify a material composition for a volume element as a relative or fractional amount of one of two predetermined material types in the volume element, and wherein the predetermined material types are optionally soft tissue and bone.

In a further aspect of the invention, which may be combined with the above aspect, the invention provides a method of configuring an X-ray image processing system comprising an X-ray imaging system and a simulator for generating simulated X-ray image data, the method comprising: generating simulated X-ray images for a plurality of samples, preferably comprising samples of at least two material types, wherein for each sample, simulated X-ray image data is generated for each of a plurality of distinct configurations of the X-ray imaging system; accessing real X-ray images for each of the plurality of samples acquired using the X-ray imaging system; for each of the configurations, fitting a transfer function between the real X-ray images and the simulated X-ray images, the transfer function defining a translation between real and simulated image data; determining a similarity metric between simulated and real images based on the transfer function for each configuration; selecting a given configuration and the associated transfer function based on the similarity metrics; and configuring the X-ray image processing system based on the selected configuration and transfer function.

The plurality of configurations may comprise one of: a plurality of distinct X-ray output settings, optionally specified as emitter voltages (e.g. kV/kVp settings); a plurality of distinct filtration settings, optionally specified as thicknesses of a filtration material used in the imaging system; and a plurality of distinct combinations of output and filtration settings. The samples may comprise material samples of a plurality of distinct thicknesses for each of the at least two material types.

The transfer function may comprise a mathematical function, preferably based on a second or higher degree polynomial. The transfer function preferably defines a translation function which varies across the image, preferably wherein the transfer function defines a respective translation for each pixel of the image (e.g. as a distinct polynomial or other function at each pixel location).

Preferably, the real and simulated X-ray images comprise intensity values specified at each of a plurality of pixel locations, wherein fitting the transfer function comprises fitting the transfer function based on logarithms of the intensity values (e.g. as a function of log(I) for intensity values I in the real or simulated images).

Preferably, configuring the image processing system comprises configuring the simulator to generate simulated image data based on the selected configuration, optionally comprising a given output and filtration setting; and/or configuring the image processing system to use the transfer function to evaluate simulated images against real X-ray images, preferably by applying the transfer function to simulated or real image data to translate image data between real and simulated image domains and/or to enable comparison of real and simulated image data.

In a further aspect of the invention (which may be combined with either of the above aspects), there is provided a method of generating composition information for a sample based on an X-ray image, comprising: obtaining an input image for processing based on a source X-ray image of the sample acquired using an X-ray detector; and determining a model of the sample based on the input image. The method comprises evaluating the model by a process comprising: computing, based on the model, simulated X-ray image data; evaluating the simulated image data against the input image to determine whether a convergence criterion is fulfilled; and generating an updated model of the sample if the convergence criterion is not fulfilled, the updated model preferably generated using the simulated image data, preferably using a scatter-corrected version of the input image generated using the simulated image data. The method may further comprise repeating the model evaluating process based on one or more successive updated models until the convergence criterion is fulfilled in a final iteration; and outputting composition information for the sample, preferably thickness and/or material composition data for respective regions or pixels of the input image, preferably based on the model of the sample used to generate the simulated image data determined to meet the convergence criterion during the final iteration. The method may further comprise any further steps or features of any method as defined above. In particular, the method in this aspect may otherwise correspond to the method in the first aspect, except that the generation of a final scatter-corrected image may optionally be omitted.

The invention further provides a system, computing device or apparatus having means, optionally in the form of a processor with associated memory, for performing any method as set out herein. The invention also provides a tangible computer-readable medium comprising software code which when executed is arranged to perform any method as set out herein.

Figure 2:
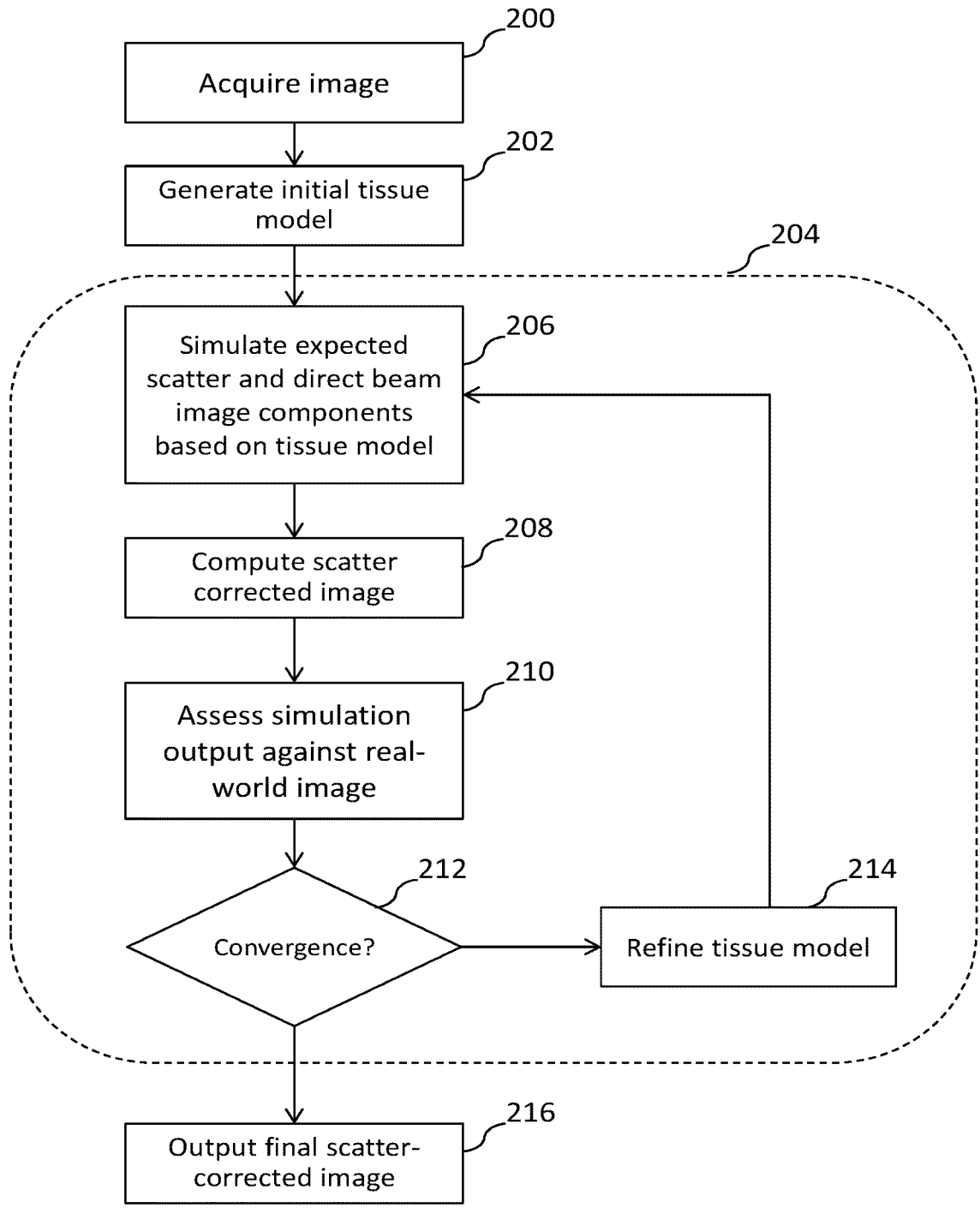
Figure 3:
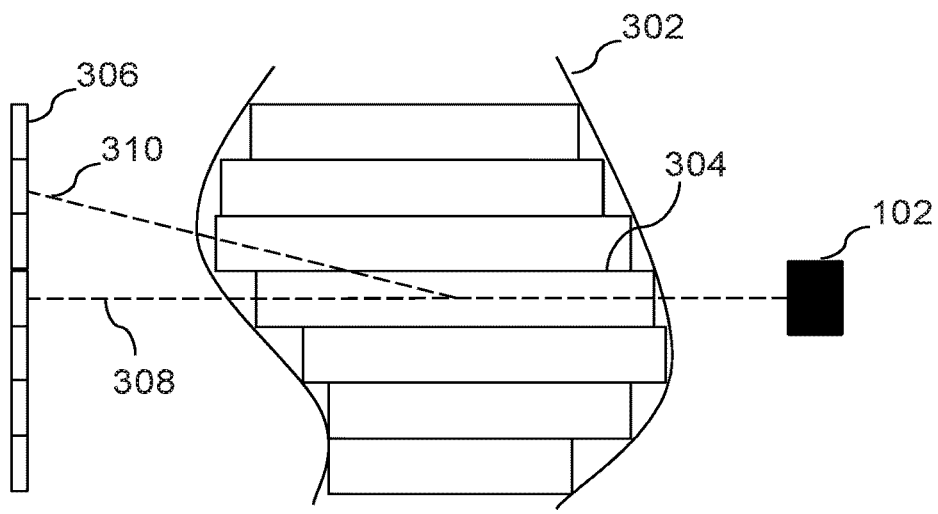
Figure 4:
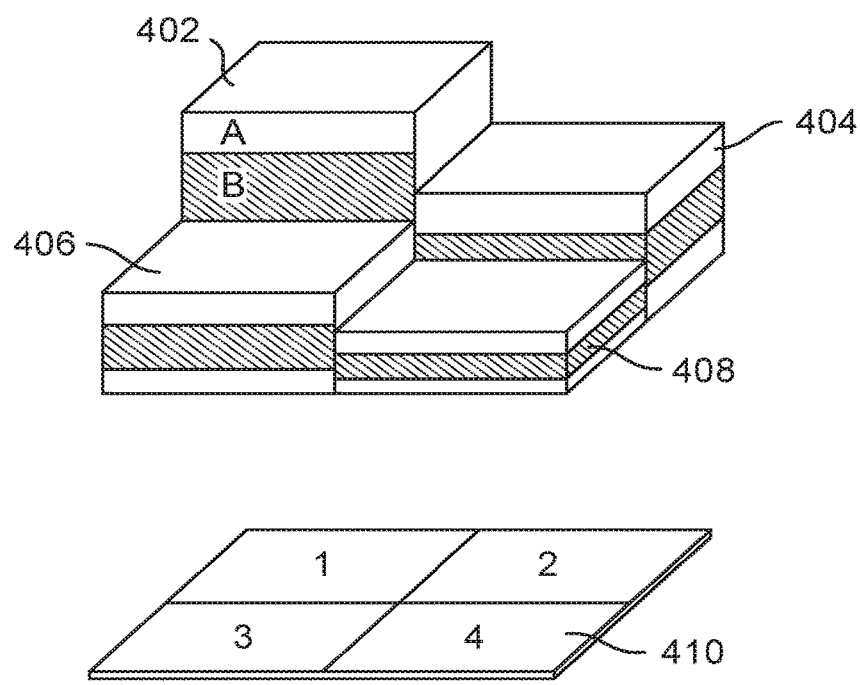
Figure 5A:
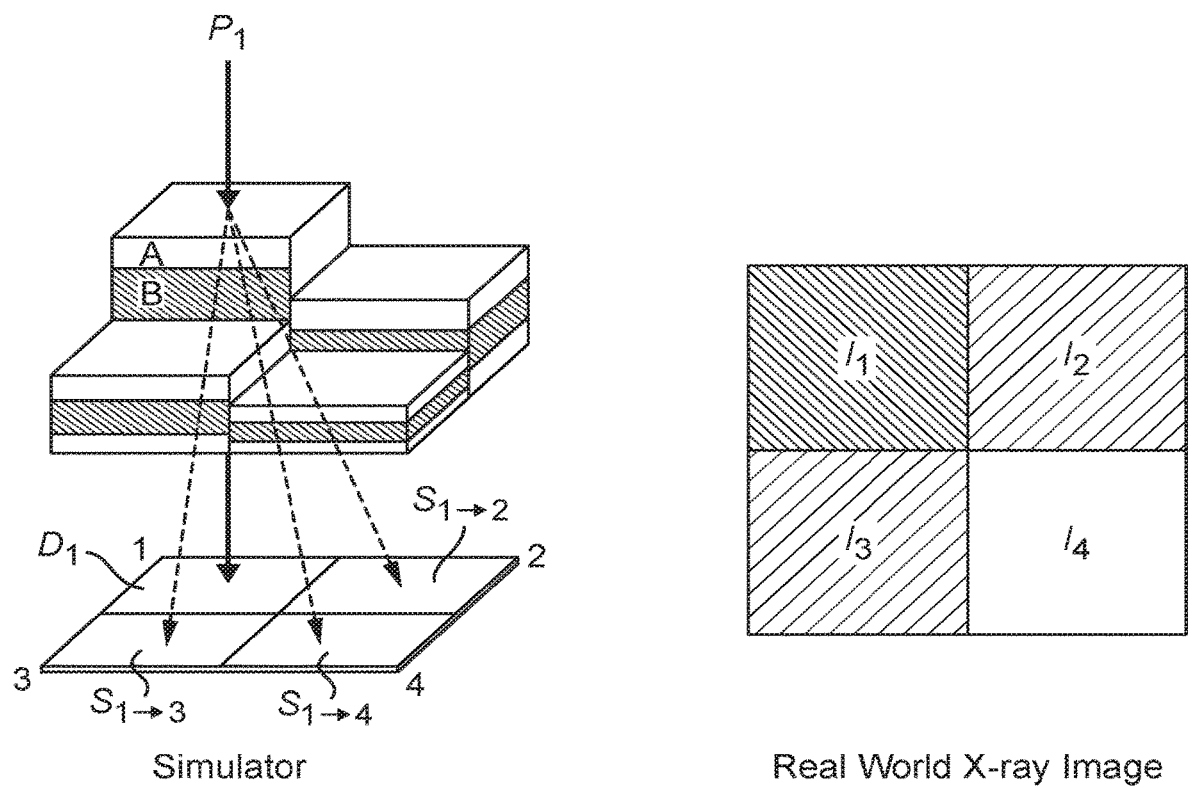
Figure 5B:
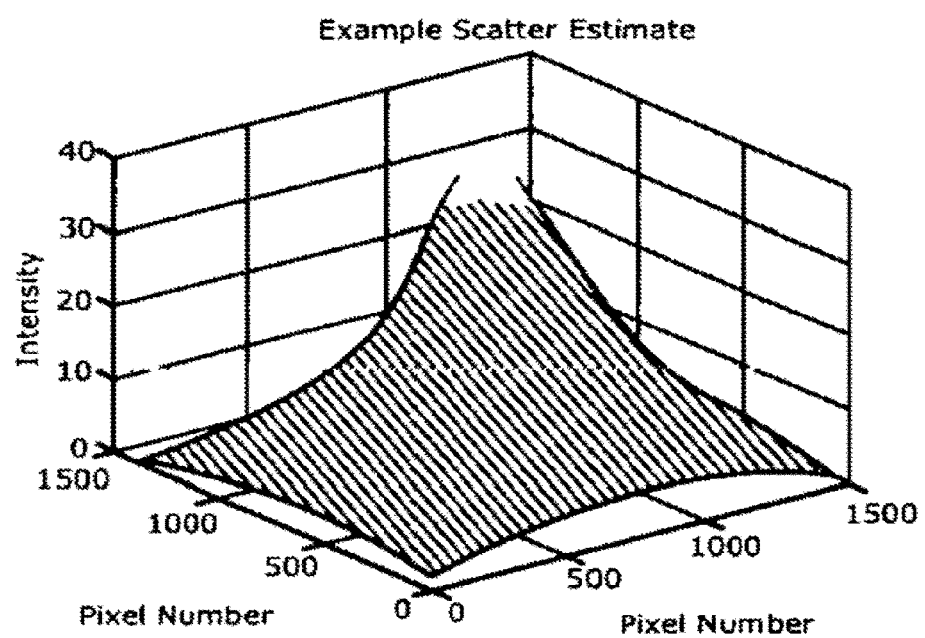
Figure 6:
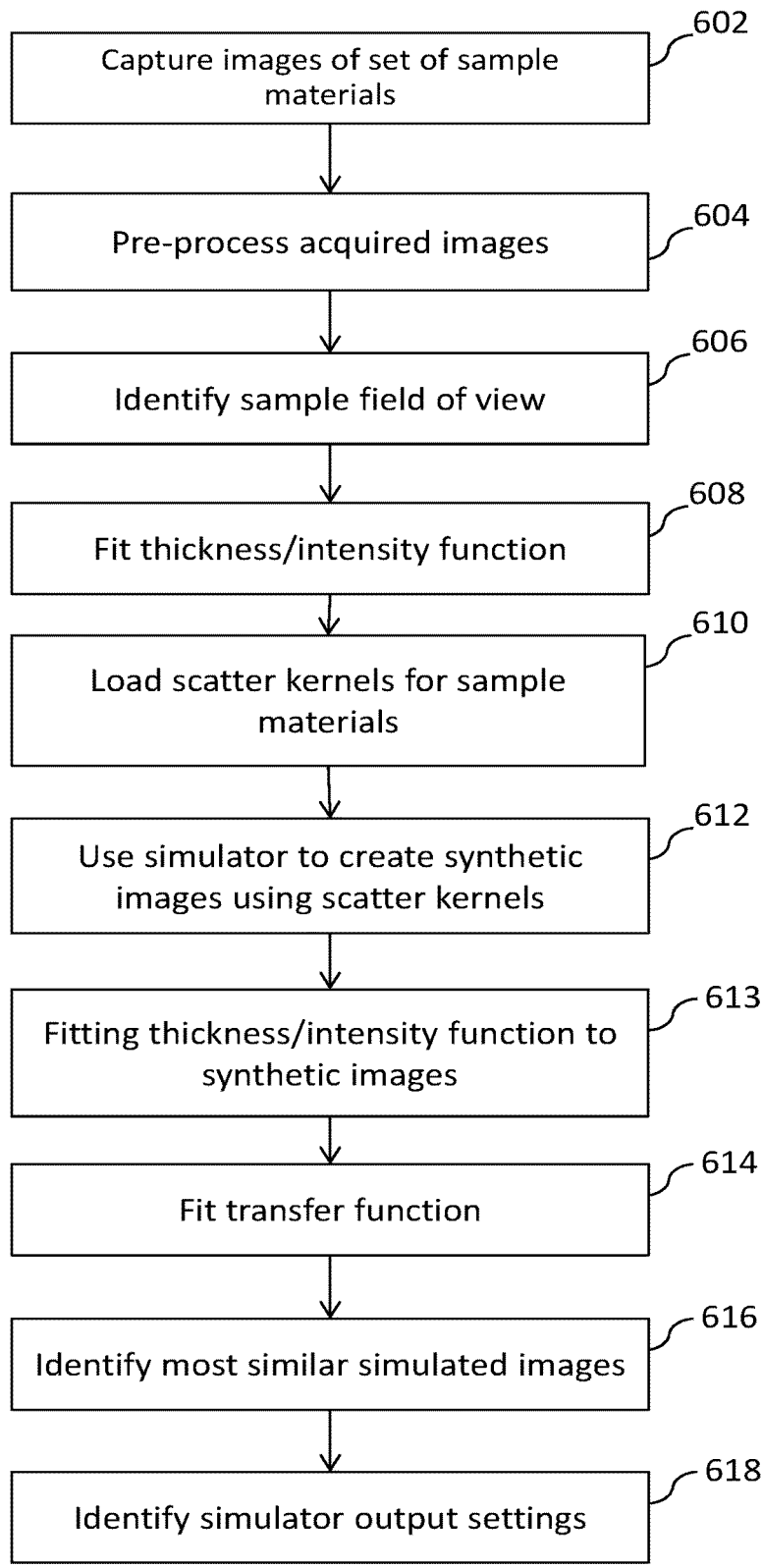
Figure 7A:
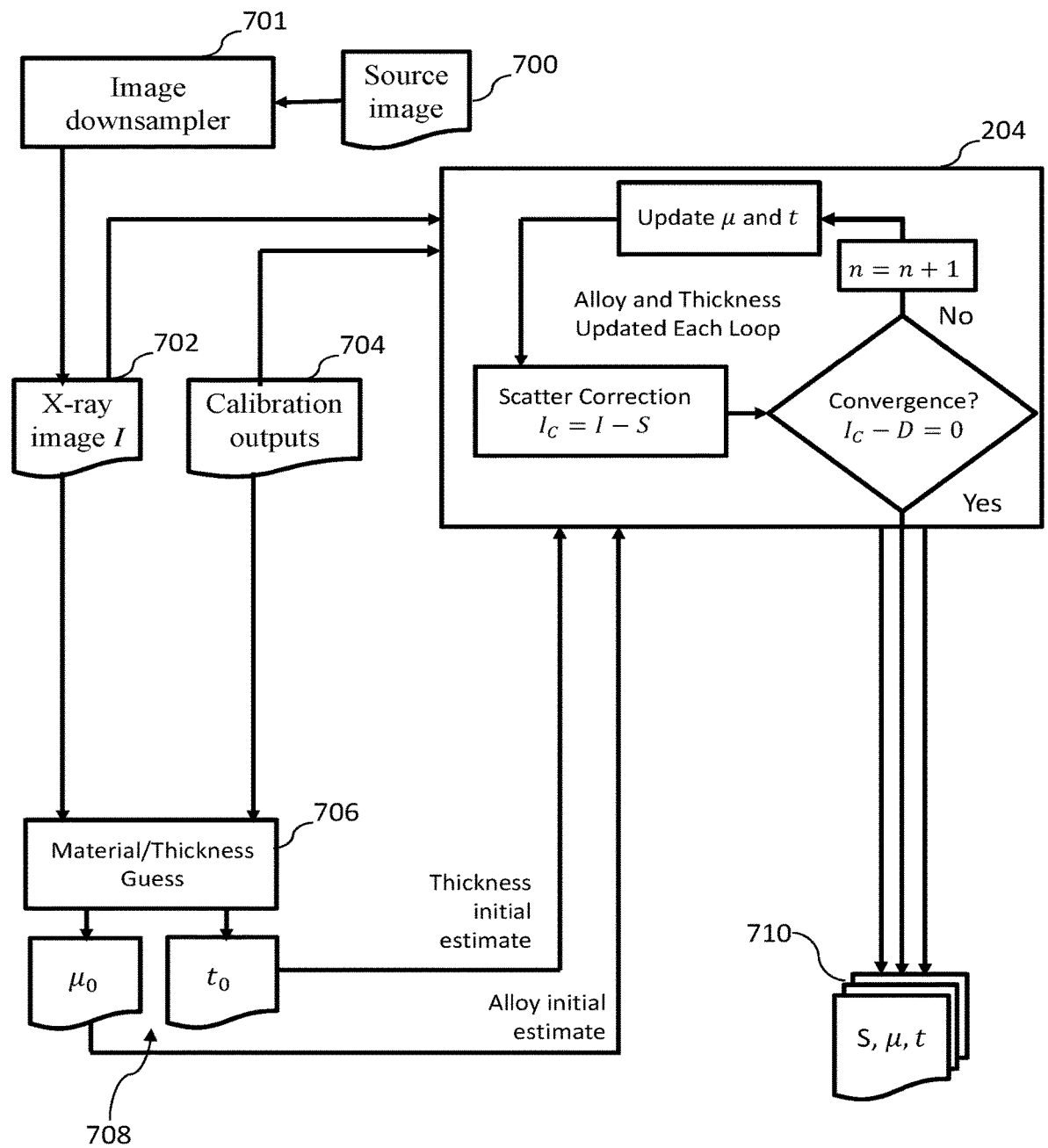
Figure 7B:
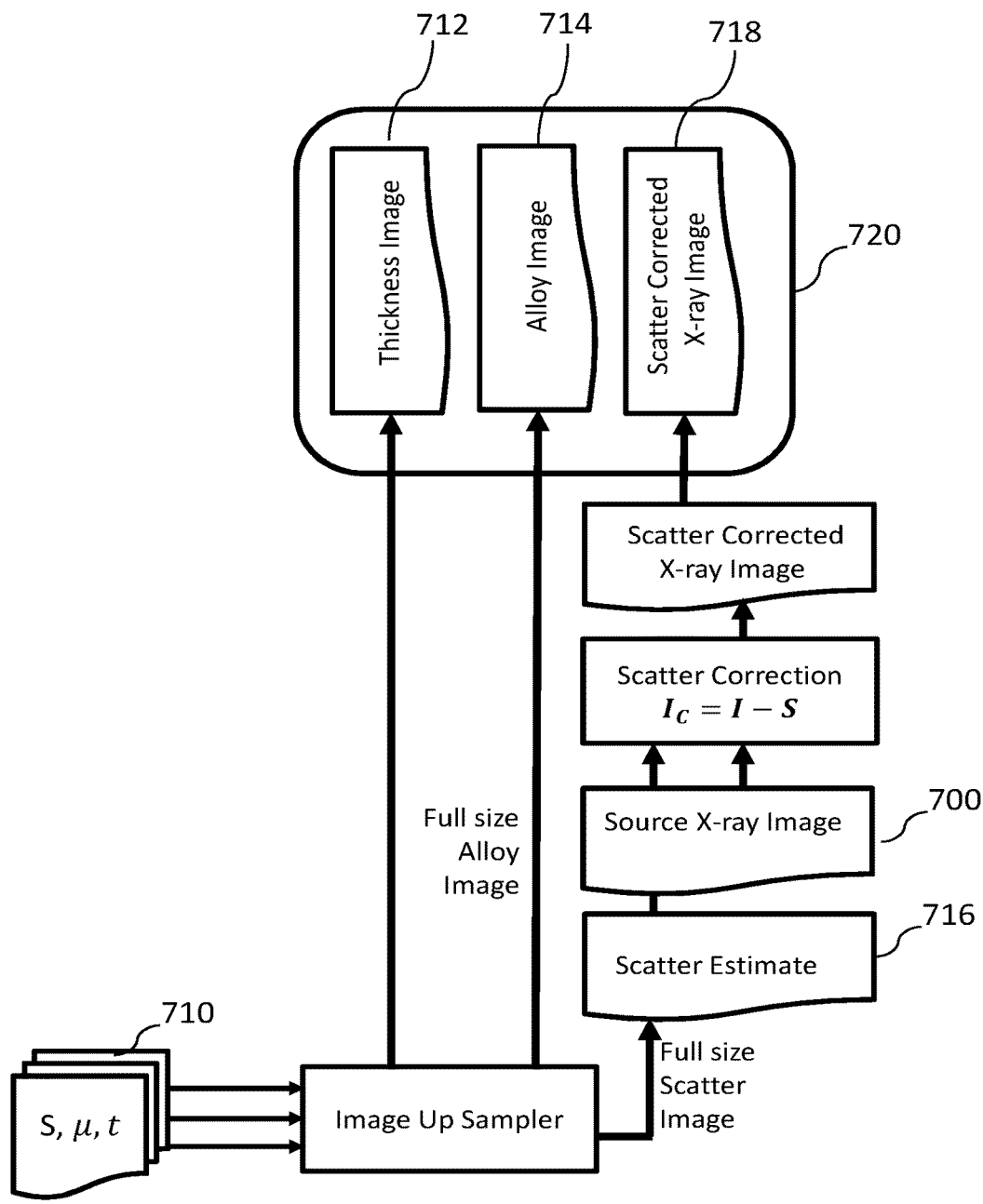
Figure 8A:
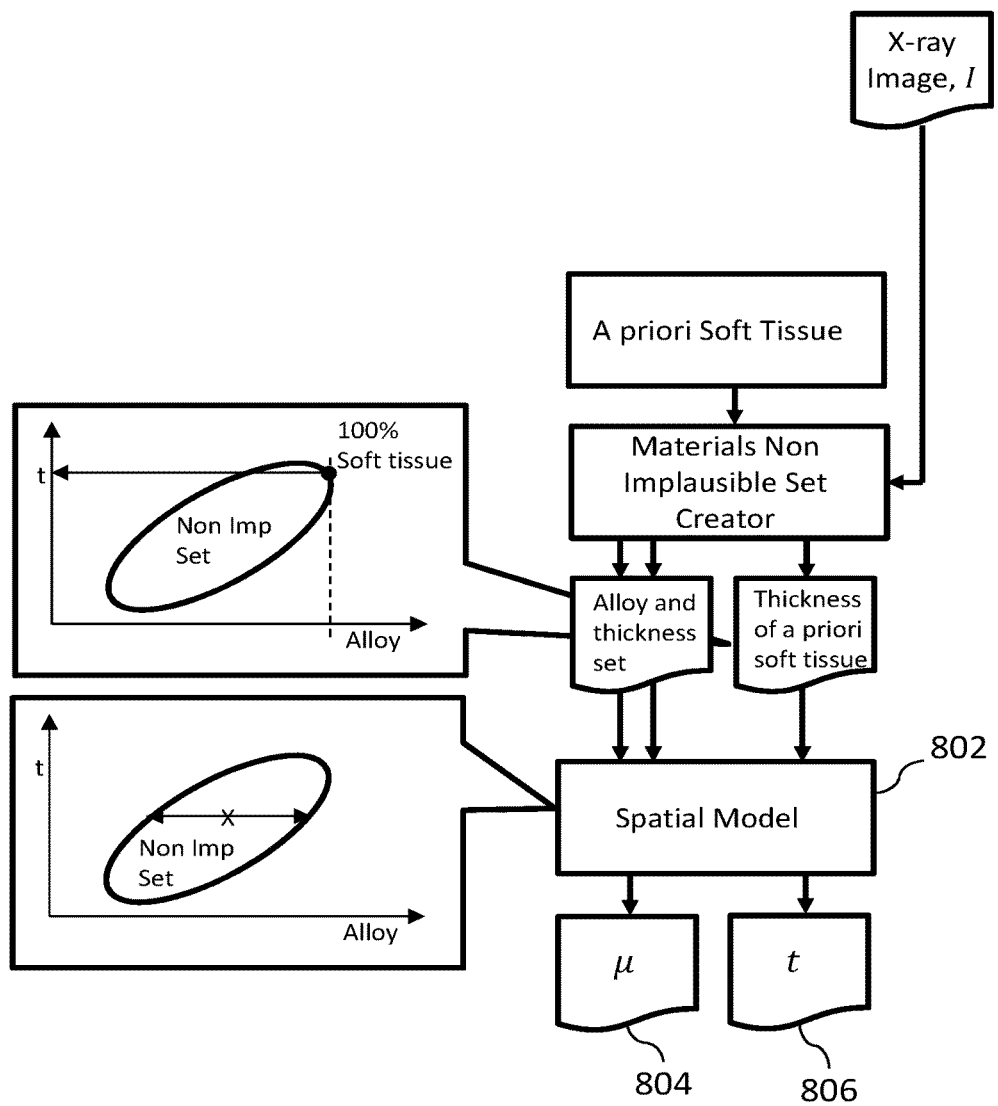
Figure 8B:
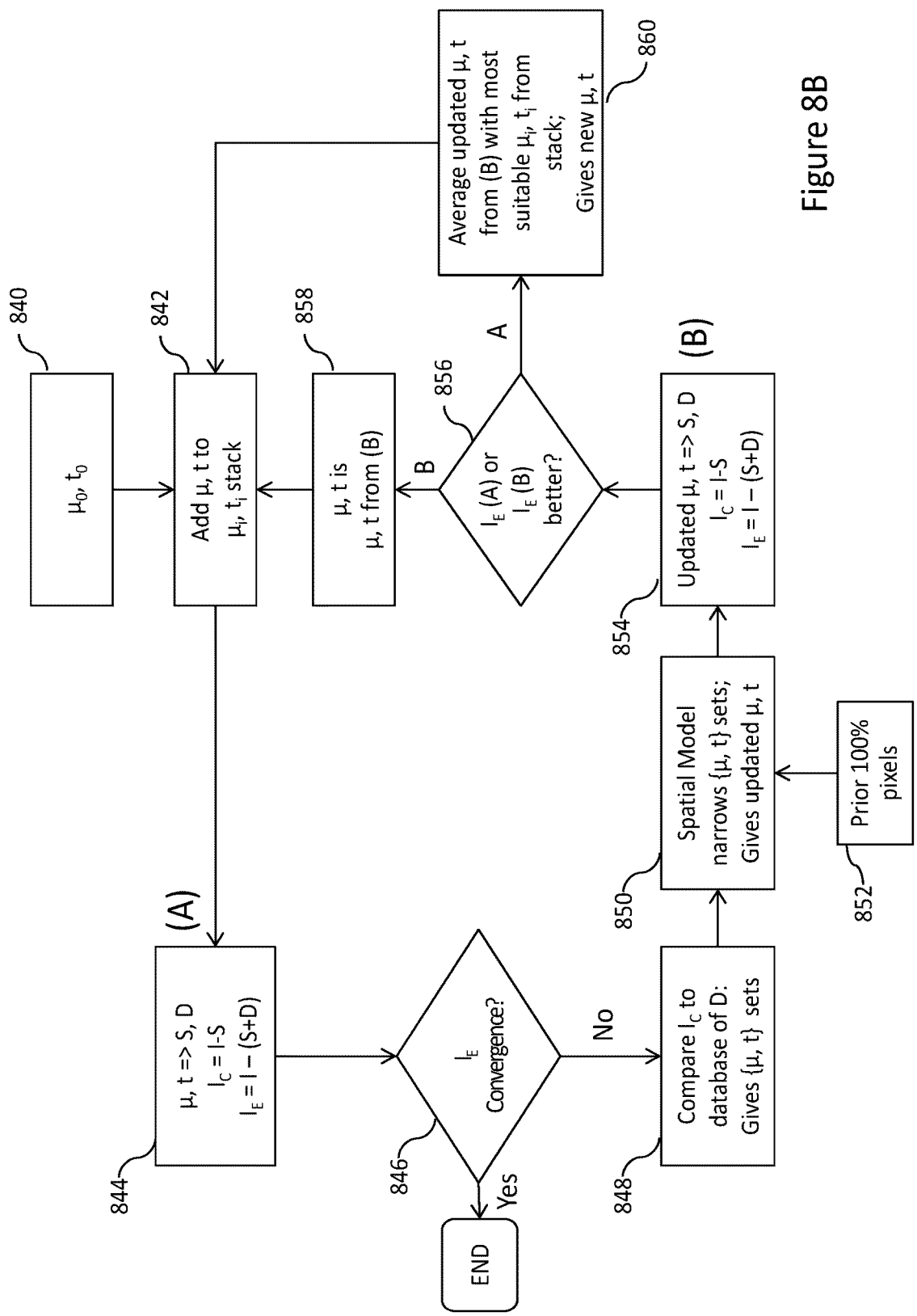
Figure 9:
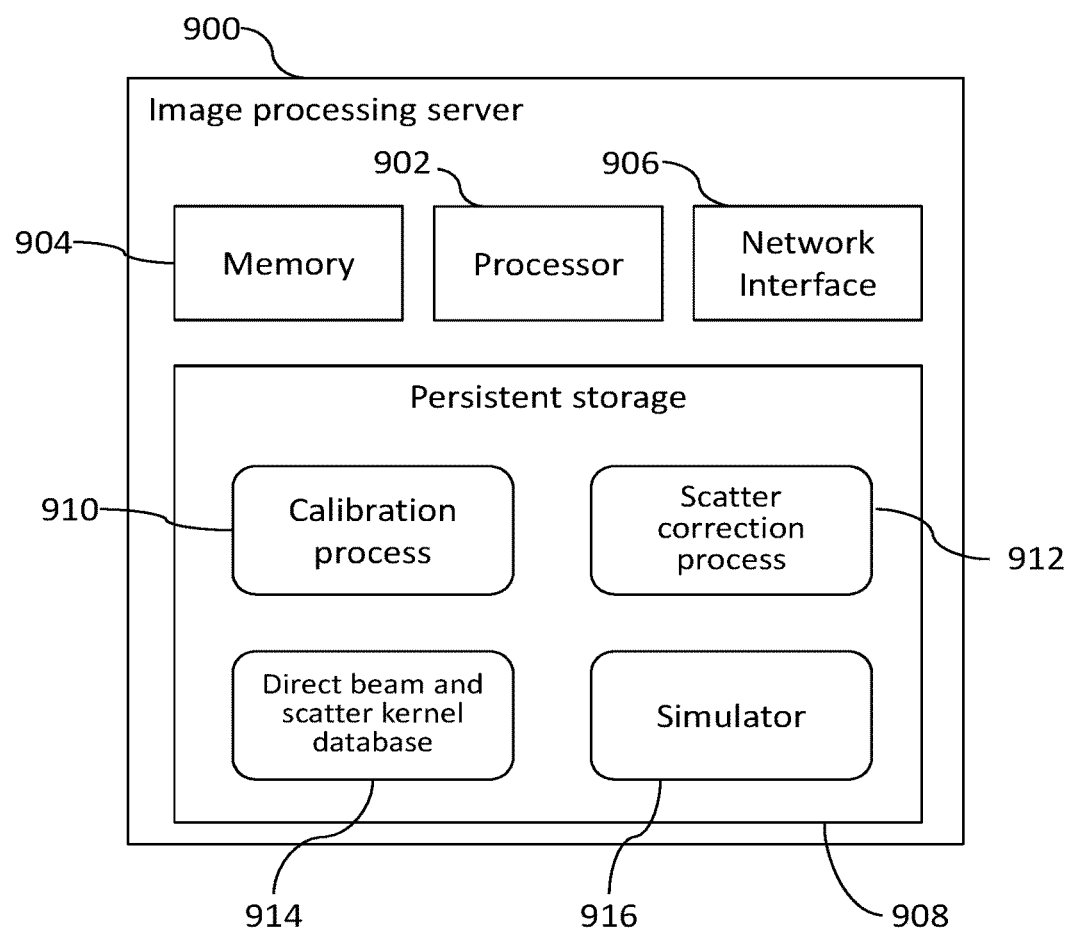

Preferred features of the present invention will now be described, purely by way of example, with reference to the accompanying drawings, in which:

FIG. 1 illustrates an x-ray imaging system in overview;
FIG. 2 illustrates a scatter correction process;
FIG. 3 schematically illustrates the imaging process;
FIG. 4 illustrates a tissue model;
FIG. 5A illustrates use of the tissue model to simulate x-ray imaging;
FIG. 5B illustrates a scatter kernel;
FIG. 6 illustrates a calibration process;
FIGS. 7A and 7B illustrate the scatter correction process in more detail;
FIGS. 8A and 8B illustrate in more detail the creation and iterative refinement of the tissue model used for scatter correction; and
FIG. 9 illustrates a computing device suitable for carrying out described methods.

OVERVIEW

Embodiments of the invention provide a system for processing an x-ray image of a subject—e.g. a patient in a medical imaging scenario—to remove image effects due to the x-ray beam being scattered by that subject. Proposed embodiments can remove the need for an anti-scatter grid and/or MAP, thereby reducing patient dose and improving image quality. Described approaches can also determine precise composition information of the subject and use this to predict and remove scatter, resulting in a more effective scatter removal method returning an image without the artefacts associated with anti-scatter grids. The described techniques can also be more flexible than using an anti-scatter grid as there are no alignment or geometric constraints.

An imaging system for implementing described techniques is illustrated in overview in FIG. 1 and comprises an x-ray source (emitter) 102 and a detector 106 for acquiring an x-ray image of a sample 104 (e.g. a biological tissue sample in the form of a human or animal subject, typically in a specific body region being imaged). In the present example the detector comprises a scintillator 108 which re-emits absorbed x-ray energy from the x-ray beam as visible light, and an image sensor 110 (e.g. a conventional CCD, charge-coupled-device, sensor) for producing digital image information based on the re-emitted light. The result is a visual image representation of the total x-ray energy incident on the detector over the x-ray exposure time. The detector typically records a single intensity value per pixel and thus the final image is essentially a greyscale image, each pixel specifying an intensity value representative of the total x-ray radiation energy incident on that pixel.

The digital image is processed by an image processing device 112 (e.g. a PC or server cluster), under control of an operator utilizing a user interface device 114 (e.g. a client workstation). Acquired and processed images are stored in storage 116 (e.g. part of the image processing device or a separate storage server).

The X-ray source 102 may be configurable to operate at a range of output settings (e.g. energy levels), for example by configuring the voltage applied at the X-ray emitter. This input voltage is also referred to as the "kV" (or "kVp", peak kV) setting since it is commonly specified in units of kilo volts (alternatively, the X-ray source may operate at a fixed kV setting). In practice, the emitted X-rays may additionally be filtered by the addition of a filtration material, typically a sheet/block of aluminium, close to the source 102, through which X-rays pass soon after being emitted and before spreading out and passing through the sample 104. This filtration is usually quoted in millimetre thickness of aluminium (Al), or equivalent thickness of Al if the material used is not actually Al. The purpose of the filtration layer is to increase the average energy of the X-rays without changing the kVp, which it does by removing low energy X-rays.

The scatter-correction process is illustrated in overview in FIG. 2, and begins in step 200 with the acquisition of an X-ray image (radiograph) of the sample (the "real" image, denoted I) using the image detector. The image may be pre-processed, e.g. by downsampling.

In step 202, an initial tissue model of the tissue being imaged is created. The tissue model provides a simplified representation of the tissue shape, composition and/or densities at different locations of the image. In particular embodiments, an initial estimate of the thickness and material composition at each pixel location is made as explained in more detail below. Note that while for clarity reference is made throughout this disclosure to a tissue model, the image sample need not be biological tissue but could be any sample or object, and thus the model may represent shape and/or composition information of any relevant material(s) of the sample. The initial model is derived from the X-ray image and thus the algorithm does not require any prior information relating to the morphology of the sample.

In step 206, the imaging process is simulated based on the initial tissue model (e.g. initial thickness and material composition estimates) to produce simulated image data. The simulated image data includes a first image component (D) representing the direct beam contribution to the final image and a second image component (S) representing the contribution of the scattered portion of the beam. Specifically, the direct beam component comprises estimated pixel data resulting from the (simulated) passage of the direct beam through the tissue (corresponding to non-scattered X-ray photons of the beam), and the scattered component comprises estimated pixel data resulting from the part of the beam that is scattered by the tissue (i.e. the scattered photons of the beam), with the extent and spatial distribution of the scattering determined based on the tissue model. These components are also referred to herein as the direct beam estimate and the scatter estimate and are represented as separate images recording the direct beam and scatter components (such that, when combined, a complete simulated image including scatter results).

The scatter estimate is then used in step 208 to compute a scatter-corrected image ($I_C$), by subtracting the scatter estimate from the real acquired image ($I_C=I-S$). This leaves a corrected version of the real image from which the simulated scatter has been removed.

In step 210, the output of the simulation is assessed against the real-world image to determine how similar the simulation output is to the real image. The comparison is based on the assumption that, as the tissue model becomes increasingly representative of the actual tissue distribution in the sample, the simulation of the imaging process will produce an increasingly accurate estimate of the direct beam and scatter components, which will result in an improved scatter corrected image.

In an embodiment the assessment is performed by computing the sum D+S of the simulated direct beam and scatter images, producing a complete simulated image, and subtracting the complete simulated image from the real world image to produce an error image ($I_E=I-(D+S)$), which indicates the difference or error between the simulation output and real image (this is of course equivalent to subtracting D and S from the original image individually, i.e. $I_E=I-S-D$). In essence, this step thus involves comparing the source image to the full simulated image (or equivalently, comparing the scatter-corrected source image to the direct beam estimate).

The error image resulting from that calculation provides an indication of the simulation accuracy and can be converted to a single value error measure in any suitable way, for example by computing a sum of error image pixels (corresponding to a sum of pixel differences across the real and simulated images). A "perfect" simulation would yield a zero error image and hence a zero result for the error measure, and thus the distance from zero in the error measure (i.e. the magnitude of the error measure since the error measure may be negative) is used to provide a measure of how well the simulated output has converged on the real image. Note, however, that both the x-ray image and the simulation are random processes so even with a perfect representation of the sample by the algorithm a minimum error related to the randomness of the real world and simulator would still be present. This limit thus typically defines the best achievable result.

A convergence criterion is used to determine in step 212 whether the simulation of the imaging process has sufficiently converged with the real acquired image. Where an error measure is used as described above, the convergence criterion may be a threshold; if the magnitude of the calculated error measure (e.g. sum of pixel differences) falls below the threshold, then the simulator can be considered sufficiently converged. Note that other approaches to comparing simulation output and real image, and other corresponding error measures and/or convergence criteria, may be used.

If the convergence criterion is not met, then the tissue model is refined in step 214. The simulation of the image process is then repeated in step 206, to produce an improved scatter and direct beam image based on the refined tissue model, with the corresponding scatter corrected image being computed and the simulation output tested against the real image as already described in steps 208-212. This iterative refinement loop (shown collectively as 204) is repeated until the convergence criterion is met in step 212 (other termination criteria may of course be used additionally or alternatively, e.g. a maximum number of iterations, maximum compute time etc.)

Once satisfactory convergence is achieved the iterative refinement ends and the final scatter-corrected image (as computed in step 208) can be output (e.g. to user interface device 114 for display to an operator) and/or stored in storage 116 for subsequent use or further processing. However, in some embodiments, as described in more detail below, the iterative refinement loop 204 operates on a reduced resolution version of the image, in which case the final scatter-corrected image may be regenerated in step 216 at full resolution, based on the final tissue model.

The above overview assumes that the outputs of the simulator are directly comparable to the real-world image but this may typically not be the case since the simulator characteristics will generally not accurately match the characteristics of the real-world imaging system. To address this, an empirically obtained transfer function is applied to the simulator outputs to make them comparable, as will be described in more detail later.

Modelling the Composition of the Sample

The simulation of the imaging process depends on a tissue model of the tissue being sampled. While a wide variety of modelling approaches could be used for modelling the distribution of different tissue types, densities etc. throughout the three-dimensional sample, a highly simplified model is preferred to allow efficient computation of the simulation results and reduce the search space for the refinement of the tissue model which occurs in step 214 of the refinement loop 204.

Thus, in an embodiment, the sample volume containing the imaged sample is divided into a set of voxels (volume elements). However, instead of a true three-dimensional array of voxels, the model in essence comprises a two-dimensional voxel array, forming a grid of m×n voxels, one voxel deep, in a plane perpendicular to the x-ray beam. This is illustrated in cross section in FIG. 3. Thus each voxel, e.g. voxel 304 in FIG. 3, extends front to back across the entire extent of the sample in the direction parallel to the beam (and thus only a single voxel is defined in that direction at each of the m×n locations of the perpendicular plane). As illustrated (in simplified form), according to the model, the beam from the x-ray source 102 passes through a given voxel 304 in a straight path, forming a direct beam contribution 308 to the pixel grid 306 of the image acquired by the detector. Additionally, the material in a voxel may scatter some of the incident beam, resulting in a scattered beam contribution 310 to the pixel grid. During simulation, direct beam contributions and scatter contributions from each voxel are computed and summed as needed to produce the complete direct beam image and scatter image respectively.

Each voxel within the sample contains a unique mixture of materials with a unique total thickness. The material composition and thickness of a given voxel determines the way in which the sample transmits and scatters incident x-rays. The intensity measured at a given pixel of the detector is a function of the material composition and thickness of the corresponding voxel of material plus the contribution due to scatter from all neighbouring voxels.

As such the intensity measured at each pixel is a function of the unique combination of materials at every location within the sample. This is a very large convolution problem with very high degrees of freedom.

To simplify the problem, the model used assumes that each voxel of material is comprised of a combination of two materials (in the present example bone and soft tissue). In the model, the percentage of each material can vary freely and the total thickness of each voxel can also vary freely.

More specifically, in a preferred embodiment, the model is implemented such that each voxel is characterised by two values:

a "thickness" value (denoted t); this indicates a thickness of the sample at that voxel (i.e. its spatial extent in the beam direction); and an "alloy" value (denoted u); this indicates the material composition of that voxel as a fraction or proportion of one of the two materials A or B relative to the total thickness, as a value between 0 and 1. In the examples herein the alloy indicates the fraction of the material in the voxel that is soft tissue.

The model further assumes a symmetric arrangement of material in the "z" direction (the beam direction, i.e. the axis along which the thickness is measured). Specifically, the thickness and alloy values together describe the voxel as a symmetric sandwich of the materials (A-B-A, e.g. soft tissue—bone—soft tissue). For example, a thickness of 10 cm and alloy value of 0.8 would suggest a simplified model of 4 cm soft tissue, followed by 2 cm of bone, followed by 4 cm of soft tissue. However, it should be understood that this is a modelling approximation (based in part on typical distributions in biological tissue samples) and will usually not be exactly representative of the real tissue distribution.

Note that in this model, the z-location (location in the direction of the beam) of the voxel is not represented (only the thickness in that direction), further reducing the problem space.

While described as a grid of voxels, since the model is one voxel deep, this could equivalently be understood as a two dimensional element grid with each element providing a tissue model (as thickness/alloy values) for that grid location.

The tissue model in this embodiment thus consists of a two-dimensional array of thickness values (also referred to as a thickness image) and a two-dimensional array of alloy values (also referred to as an alloy image). The dimensions of the thickness and alloy images correspond to the pixel plane of the acquired image. However, to reduce computational complexity, the tissue model resolution may be reduced compared to the resolution of the original image acquired by the X-ray detector (and hence the process depicted in FIG. 2 may operate on a downsampled version of the original acquired image, at the same resolution as the tissue model). The alloy and thickness images can essentially be thought of as the outputs of two additional, lower resolution detectors occupying the same space as the X-ray detector, that give values of alloy fraction (unit-less) and thickness (e.g. in cm) respectively rather than intensity.

Thus, references to the "tissue model" in the following shall be understood to refer to a model as described above, comprising arrays of thickness and alloy values describing material shape/composition across the image plane of the source image (but typically at lower resolution). However, other approaches to modelling tissue could be employed, for example representing each voxel as an A-B-A tissue sandwich with explicitly defined material thicknesses, or as a three-dimensional voxel array with voxels having individual alloy values, etc. Furthermore, models with a single material type (e.g. modelling only thickness of each voxel, each voxel assumed to consist entirely of a single material), or models with three or more material types could be used, e.g. defined by multiple material fractions or other structural information per voxel (at the cost of increased computational complexity). In other examples, constant thickness may be assumed (or known/measured) for the entire sample, with only material composition defined for each voxel of the model. The term "tissue model" thus encompasses any suitable representation of the arrangement of material in a sample, the shape of the sample, the distribution of tissue types (or other material types) and/or of tissue/material densities in a sample.

Simulation

FIG. 4 illustrates the tissue model using a simplified case with four voxels of material 402, 404, 406, 408, and four corresponding simulated output pixels 410.

The model assumes each voxel of the sample to be comprised of two materials, "A" (e.g. soft tissue) and "B" (e.g. bone). The overall thickness of each voxel, as well as the thickness of each material, $t_A$ and $t_B$ can vary from one voxel to the next. Here we assume that we know the materials A and B and we know the individual thicknesses, $t_A$ and $t_B$ for each voxel. In the simplified model described above, each voxel is characterised by the total thickness and the alloy value which specifies the proportion of material A within the voxel, providing equivalent information on the assumption of a symmetric sandwich structure.

Based on the geometrical and material information in the model, the x-ray interactions with this sample and the detector are simulated using a Monte Carlo model. The outputs of the simulator are calibrated to the outputs from the real world imaging system by application of a transfer function (as will be described in more detail later), which allows the outputs of the simulator to be applied directly to the real world image. In other words the simulator and real world information become interchangeable.

To create a simulated x-ray image of the sample, the simulator sums up a series of pencil beam $P_1$, $P_2$, $P_3$ and $P_4$. Here a pencil beam is defined as a collimated beam of x-rays with zero degrees of divergence.

FIG. 5A shows the case where pixel 1 is irradiated with a pencil beam, $P_1$.

This can be repeated for each pixel in order to produce scatter kernels $K_1$, $K_2$, $K_3$ and $K_4$. The simulated intensity at each pixel is then given by the convolution of all scatter kernels. As shown in FIG. 5A, the scatter kernel is a point spread function, containing direct and scatter x-rays. In the case of pencil beam $P_1$ there is a direct component, $D_1$, incident on pixel 1 and scattered components $S_{1 \to x}$, emanating from pixel 1 to pixels x=2, 3 and 4. FIG. 5B provides an illustration of a more realistic higher-resolution scatter kernel.

The intensity recorded at each pixel is therefore the direct beam at a given pixel plus the scatter contribution from every neighbouring pixel:

$$\begin{bmatrix} I_1 \\ \vdots \\ I_n \end{bmatrix} = \begin{bmatrix} D_1 + S_{2 \to 1} + S_{3 \to 1} + S_{4 \to 1} \dots S_{n \to 1} \\ \vdots \\ D_n + S_{1 \to n} + S_{2 \to n} + S_{3 \to n} \dots S_{n-1 \to n} \end{bmatrix} \quad [1]$$

Given that we have calibrated our simulator to the real world, the convolution of kernels $K_1$, $K_2$, $K_3$ and $K_4$ will produce an image, $I_{sim}$, which resembles that of the real world x-ray image, I within a margin of error, $\varepsilon$.

$$I_{Sim} + \varepsilon = I \quad [2]$$

The system uses the Monte Carlo truth to separate out the contribution into each pixel due to scatter and the contribution into each pixel due to direct beam as illustrated in equation [1]. From this, a simulated direct beam image, D, and a simulated scatter image, S are generated.

The scatter corrected real world image, $I_C$, is then calculated by:

$$I_C = I - S \quad [3]$$

Note that these examples assume a straight line beam passing through each voxel but corrections could be made for a non-straight beam, e.g. a beam spreading from a central source resulting in a beam path with different angles through different voxels.

An accurate simulation would of course require full knowledge of the thickness and materials composition of each voxel which would generally not be available in a real world sample. Instead, embodiments may use a simplified modelling approach which considers all possible combinations of the two materials A (e.g. soft tissue) and B (e.g. bone) for each voxel. With sufficient computational power the x-ray image arising from each of these combinations can then be simulated. The best combination of materials and thicknesses across all pixels can then be evaluated using equation 4. The minimum value of $I_E$ relates to the simulated image which most closely matches the real world x-ray image, where $I_E$ indicates the simulation error:

$$I_E = I - I_{sim} \quad [4]$$

The model sample composition which minimises the magnitude of $I_E$ across the image (i.e. that is closest to a zero image) is the closest estimation we can produce to the real world, given the errors associated with our calibration of the simulator to the real world and the stochastic nature of both the simulator and real world measurements.

Using this approach it is possible to see that it would in theory be possible to understand the sample composition and x-ray interactions using only a Monte Carlo model and a calibration of the simulator to the real world.

Once an acceptable minimisation of $I_E$ has been found (e.g. based on a convergence threshold as discussed above)

then the system has converged on a reasonably accurate knowledge of the tissue model of the sample and how x-rays interact with it.

One difficulty with this approach is the problem of high dimensionality i.e. the number of possible solutions that need to be evaluated using equation 4 is very large. Thus, to reduce the search space, embodiments of the invention adopt the following strategies:

1. Deriving an initial tissue model as a starting point for the iterative refinement process, based on image features of the original acquired image. In particular, this involves deriving initial estimates for alloy and thickness model parameters (in an example this is done based on a prior classification of pixels which have an alloy value of 1, i.e. 100% soft tissue composition),
2. Iterative refinement of the tissue model (specifically the alloy and thickness estimates) guided based on observed improvement of the simulated x-ray image (see step 214 in FIG. 2)

These two components will be described in more detail later.

Generation of Simulated Direct-Beam and Scatter Contributions by the Simulator

In one approach, an approach based on ray-tracing could be used to generate the direct beam and scatter estimates, by computing the paths of x-rays through the material based on a given 3D model of the subject (e.g. derived from the tissue model). This may involve building the given 3D model of the sample in the Monte Carlo simulator and then simulating the direct and scatter components for each pixel location. However, this approach would typically be very computationally demanding (especially given that the simulation may be repeated many times during the iterative refinement of the tissue model, and given that this approach may necessitate using divergent beams to simulate the x-ray image arising from a given sample, rather than pencil beams which reduce the number of events to be simulated).

Embodiments of the invention thus provide an alternative, more efficient approach to the creation of the simulated x-ray image. The approach is based on efficient creation of non-stationary non-symmetric kernels, by combining precomputed symmetric kernels for specific material combinations.

In an embodiment, a Monte Carlo simulation package called GEANT4 is used to simulate X-ray interactions. As described above, this involves simulating pencil-beams so that the way in which the sample scatters can be observed. X-rays are created at the source as a narrow beam directed at a pixel on the detector denoted the "central pixel". X-rays which are not scattered will hit the central pixel.

While in principle, simulation could be performed "online", during the iterative refinement loop 204, this may be computationally very demanding. To reduce the computational burden of simulation, an alternative approach performs simulation "offline", i.e. prior to running the iterative refinement. In this approach, simulation is performed in advance for a predefined set of alloy and thickness combinations ($\mu$, t) to obtain a set of scatter kernels for each ($\mu$, t) combination (e.g. across defined ranges and step sizes of $\mu$, t values). The resulting scatter kernels are stored in a database. In certain preferred embodiments, the predefined set of parameters for which scatter kernels are stored in the database is chosen to be a sparse mesh which can later be interpolated for any desired $\mu$, t combination.

In an embodiment, unless simulating the effect of only air, the simulation places a sample in the path of the X-ray beam. The sample consists of a cylindrical core with a given radius (e.g. 1um) of one material surrounded by an annulus of another radius (e.g. 50 cm) of another material. This allows the system to simulate what it is like to scatter in one material and then immediately continue the rest of the path to the detector in another material. Embodiments may generate scatter kernels for different combinations of core and annulus compositions (alloy) and/or different combinations of core and annulus thicknesses (in an alternative embodiment a common thickness may be specified for core and annulus). For example, simulations may be performed from 1 cm to 20 cm in steps of 1 cm for overall thickness, 0% to 100% in steps of 10% for the core alloy value and 0% to 100% in steps of 10% for the annulus alloy value—this example would mean there would be 20*11*11=2420 simulations required for direct beam and scatter kernels. The central pixel of the simulation is the direct beam value and everything else is the scatter kernel (though for convenience the direct beam value may be recorded as the central pixel of the scatter kernel).

The precomputed scatter kernels are then used subsequently to obtain simulated image data. This involves modifying the shape of the kernels according to the 2D ray path; in particular, the intensity of the tails of the kernel is modified according to the 2D voxels in the tissue model, as described in more detail below.

Specifically, during the iterative refinement process 204, in particular the simulation step 206, the system looks up the relevant direct beam values and scatter kernels for each pixel of the tissue model and generates simulation results by convolving (e.g. summing) the scatter kernels and separating the direct beam and scatter components as previously described. Additional scatter kernels not generated by the simulation may be produced by interpolation of adjacent scatter kernels (this is also referred to as emulation rather than simulation of the scatter kernel). Such interpolated scatter kernels can be generated in advance (and stored in the database), online during operation of the process 204, or both. Thus, references to simulation herein include making use of pre-calculated simulation results when generating simulation output.

In more detail, during the iterative refinement loop, for given estimates of $\mu$,t, the stored direct beam values in the database can be used to get the corresponding estimate for direct beam at a pixel for any given combination of $\mu$,t. Repeating this process for every pixel of our $\mu$,t alloy and thickness estimates and writing the intensities in to the corresponding pixels produces the direct beam estimate D. Note that for both scatter and direct beam, the system does not make corrections for a divergent beam, choosing instead to treat each pixel as if it had its own independent source so incident rays to different pixels are parallel to each other. The further away the source is from the object, the less of an issue this is, though other embodiments could apply corrections for this if required.

The scatter estimates may be obtained as follows. The aim is to obtain the scatter kernel caused by the sample at any given pixel (x,y). To know what intensity the kernel has at pixel (x', y') when scattering from pixel (x,y), the scatter lookup database is used. First, the kernel scatters from pixel (x,y) with (a) alloy $\mu$ with (b) thickness t. It then travels through (c) an average alloy $\mu_r$ for (d) a distance r (where the average is determined from the alloy values of voxels on the path from x,y to x', y' as specified in the tissue model). The system identifies the intensity corresponding to these four values and interpolates from the scatter lookup table in the database if it does not exist. This is done for every pixel the X-ray could scatter to (x', y') and every pixel an X-ray could scatter from (x,y). Summing up all these values gives the scatter estimate. Further improvements to calculating the intensity of the scatter could be made, such as including the effect of (e) the average thickness $t_r$ the ray travels through but such improvements add another dimension which may be computationally expensive and adds further processing time.

Matching the experimental setup described in relation to FIG. 1, the simulator is configurable in terms of the input energy level (peak kV) and the applied filtration (specified as Al thickness in mm). Where scatter kernels are pre-calculated, this may thus be done across a range of energy level and filtration values, with the scatter kernel database storing the scatter kernels for the different simulator settings.

Calibration

The refinement loop described above relies on comparison of the simulated image data to the real-world acquired image to determine when the simulation—based on the tissue model of the imaged tissue—is considered sufficiently accurate that the simulated scatter estimate can be used for scatter-correction of the real acquired image.

A calibration process is performed to ensure comparability of the real imaging output of the detector and the simulated imaging output of the simulator. Calibration involves determining a transfer function which can be applied to the simulator output to make it comparable to the real-world image (equivalently, an inverse of that transfer function could of course be applied to the real-world image for comparison to the simulator image).

In preferred embodiments, the simulator is based on a Monte Carlo model, and the purpose of calibration is to match the behaviour of the Monte Carlo model to the observed real world behaviour. More precisely, the purpose is to match the underlying energy spectrum between the model and the real world. This is carried out using an indirect method as it is typically difficult (and requires costly additional equipment such as a multi-spectral detector) to observe the energy spectrum in the real world.

The calibration process is based on the assumption that, by identifying suitable parameters for the model which provide a material-invariant transfer function between the simulator output and the real world output, then the underlying energy spectrum of the real world imaging system has been matched to within random error. This is considered a reasonable assumption because different materials have different energy-dependant attenuations of x-rays and hence the only way in which the simulator output can match the real world for more than one material is if the energy spectrums match.

The calibration process is illustrated in FIG. 6.

Calibration starts (step 602) with capturing a set of real world images of at least two different materials, each with a number of different thicknesses. In an embodiment, images of flat blocks of PMMA (polymethyl methacrylate or perspex) and aluminium at 5 different thicknesses are captured, plus an image with no sample in the beam. Example thicknesses are:

PMMA: 5, 10, 15, 20, 25 cm
Al: 1, 2, 3, 4, 5 cm

Thicknesses are selected in order to span the range of attenuations which can be expected to be encountered in the samples that are to be imaged. Also the attenuation range of the two materials should preferably be approximately matched.

In step 604, the acquired images may be pre-processed to make them more suitable for subsequent processing. For example, the raw images may be gain- and offset-corrected.

In step 606, the sample field of view is identified. This is the region of the detector which is illuminated by x-rays. The field of view is the only region considered as being the origin of scatter so this marks the boundary of where data processing is performed. All regions outside of this field of view are ignored. In some embodiments, when actual test samples are processed, the collimation can be smaller than that defined by the field of view but not larger, though this restriction may be removed in other embodiments.

In an embodiment, it is assumed that in calibration the X-ray images will appear either as a "flat" image if the entire detector was hit by direct X-rays or as an illuminated rectangle surrounded by a shadow if a collimator was used. The field of view (FoV) is thus defined using a logical image with 0 for pixels which were in the collimated region and not hit by direct X-rays and 1 for pixels which were hit by direct X-rays. A corresponding reduced resolution (sub-sampled) version of this image is created for use in the simulation. The FoV image can either be found by a simple threshold of the image where all pixels above a given intensity are 1 and all those below are 0. Alternatively, edge detection methods can be used. In calibration, a transfer function can generally only be found at illuminated pixels as no information is available at dark pixels (according to the FoV).

In step 608, the system fits a function to the source image data f(thickness)=log(I), where I is the average intensity over repeated frames of the sample images. The function is fit for every pixel in the field of view. Working in log(I) space makes emulation easier and keeps the values to roughly the same order making calculations on a computer more numerically stable.

In step 610, a prebuilt calibration training database is loaded. This is comprised of scatter kernels for each of the materials measured in the real world across a predetermined set of kV values and filtrations. These values cover a predetermined range of kV and filtration values in predetermined step sizes. The ranges may be chosen depending on the real world system settings of the detector setup. Purely by way of example, if the user intends to run the real world system at 80 kV with roughly 2 mm filtration, the simulation may use kV values ranging from 70 k V to 90 kV in steps of 1 kV and filtration of 0 mm to 5 mm in steps of 0.25 mm. On the other hand, if the system is run at 60 kV, a range of 45 kV to 75 kV may be used in the simulator. The ranges can be narrowed or widened depending on familiarity with the system In step 612, synthetic images of the same size as the real world images are created by convolving the scatter kernels together. This step is performed for each kV and filtration value, using the scatter kernels for the given kV and filtration, and for the relevant material. Thus, the synthetic images are created for each material, at each thickness, at each filtration and kV combination. Each synthetic image represents a block of constant thickness of a single material, just like the real world set of images obtained in step 602. The aim is to reproduce the real sample images in the simulator.

In step 613, a thickness/intensity function is fit for the synthetic images in the same way as done is step 608 for the source image in step 608.

In step 614, the system then fits a transfer function between the real world images and the synthetic images for each kV and filtration value in the kV and filtration ranges.

The purpose of the transfer function is to take up any remaining discrepancy between the simulator and the real world. The underlying assumption is that if the energy distribution of the model has been matched to the real world then there will only be scalar discrepancies between the model and the real world, or in the worst case the discrepancies may be invariant to the sample material.

In one implementation, each pixel has its own transfer function which is a quadratic function. All of the transfer functions are stored as a 3D array of size nr*nc*3 where nr and nc are the number of rows and columns according to the pixel/voxel resolution used for deriving the tissue model in the FIG. 2 process, and the third dimension is three, holding the three parameters for the quadratic function. The fitting process involves using the simulator to reproduce the real world calibration samples in the simulator space. The function is built by fitting log(I) in the real world as a function of log(I) in the simulator. However, other forms of transfer function could be used (e.g. using transfer functions based on functions other than quadratic functions, e.g. higher-order or lower-order polynomials; preferably a polynomial of at least second degree is used).

In step 616, the system identifies the set of synthetic images which are most similar to the real world in terms of an implausibility metric. This provides a non-implausible set and defines all of the kV and filtrations which can be used in the simulator to match the real world output within the errors associated with the real world and simulator measurements. The implausibility metric is a measure of similarity between a real world observation and a simulator output (usually similar to the Mahalanobis distance). This step produces a set of non-implausible solutions rather than a single solution due to the fact that there are two random processes (simulator and real world). As such all solutions can be deemed non implausible given the error.

In an embodiment, the implausibility metric for selecting kV, filtration and transfer functions is that the maximum distance between the real world log(I) curve and the transferred log(I) curve from the simulator cannot be more than a distance of 2 scaled by an uncertainty. This typically means that many transferred log(I) curves from the simulator (each at a different kV and filtration) will be sufficient up to the given uncertainty at the time, providing a non-implausible set.

In step 618, the system identifies the lowest implausibility transfer function, kV and filtration. These kV and filtration values, together with the transfer function, are then defined as the simulator output settings.

Detailed Description of the Scatter Correction Algorithm

FIG. 7A provides an overview of the process for generating and iteratively refining the tissue model in accordance with an embodiment. The process is based on an input x-ray image 702, along with the outputs of the calibration process described previously, in particular the database of scatter kernels and the transfer function.

A sub-process 706 establishes an initial estimate (or guess) of the tissue model, specifically the material composition (alloy) and thickness for each voxel. Determination of the initial tissue model estimate will be described in more detail later. This produces a pair of values for each voxel, po and to. Ho is the alloy value characterising the material composition for the voxel and in a preferred embodiment indicates a proportion (e.g. as a fractional value or percentage) of soft tissue within the voxel (or vice versa; instead of a fractional value of one tissue type, a ratio of the two tissue types could also be specified). More generally this could indicate proportions or ratios of any two tissue or material types depending on the nature of the subject being imaged. $t_0$ characterises the thickness of the material at that voxel. The zero subscript indicates that these are initial estimates of the relevant values prior to iterative refinement of the tissue model.

Since the model assumes that the bone material is centrally located and surrounded by soft tissue, the thickness t and alloy µ together completely characterise the three layer tissue model for a given voxel (as depicted in FIG. 4). Note throughout this description the terms t and µ are used as shorthand for an array of such values, it being understood that there is one set of t and µ values for each voxel/pixel. As will be described in more detail below, the initial tissue model estimate is based on an a priori soft tissue classifier which classifies image regions based on pixel intensities.

The iterative refinement loop 204 uses the initial thickness and alloy estimates as a starting point for analysing the input image 702. As described previously, the direct beam and scatter components are estimated by simulating x-ray interaction using the initial estimated tissue model. Generation of the direct beam and scatter estimates involves translating the simulator output using the transfer function derived by the calibration process (essentially translating simulated image data into the domain of the real x-ray image data), to ensure the simulated data can be evaluated against the real x-ray data of the input image 702 (alternatively a corresponding inverse translation could be applied to the real x-ray data 702). It will be understood that the transfer function is used to enable comparison/evaluation of real and simulated image data and use of the transfer function should therefore be understood as implicit even where not explicitly mentioned.

The scatter estimate is used to perform scatter correction of the input image to produce a corrected image $I_C$. In this example, convergence is checked by comparing the scatter-corrected image to the direct beam image (indicated in shorthand as $I_C-D=0$; however, in practice complete convergence may not be achievable, and instead the process preferably tests whether the difference between the scatter-corrected image and the direct-beam simulated image is below a threshold where the threshold is determined by the estimated errors). As previously described, the convergence test may equivalently compute a complete simulated image from direct beam and scatter components and compare this (by subtraction) to the input image.

If the convergence criterion is not met, the tissue model (i.e. the u and t values for each voxel) are updated and the loop is repeated, by regenerating the simulated direct beam and scatter components using the updated tissue model. Once the convergence criterion is met, the process ends, and the final tissue model µ, t and scatter estimate S are provided as output 710.

Note that for computational efficiency, the tissue model is preferably at a lower resolution than the source image 700 acquired by the detector and thus to match the tissue model resolution the input image 702 is generated by downsampling (701) the original high-resolution source image 700. Operating at reduced resolution can significantly reduce the search space when refining the tissue model and reduces the number of elements required in the scatter kernel convolution.

FIG. 7B illustrates processing applied to the output of the iterative refinement loop. The outputs 710 may be scaled to the original image resolution to produce full resolution thickness and alloy images (or maps) 712, 714 and a full resolution scatter estimate 716. This may be achieved by upsampling the scatter estimate and the thickness and alloy images. The upscaled scatter estimate 716 is then used to perform scatter correction of the full resolution source X-ray image 700 (by subtracting the scatter estimate from the source image), to form the final scatter corrected x-ray image 718.

In an embodiment, the alloy and thickness estimates are not simply upsampled to the full original resolution as is done to obtain the scatter estimate. The scatter estimate is a low frequency function and thus simple upsampling can be effective; however, the materials information represented by the tissue model is not generally as low frequency as the scatter estimate. Thus further post processing is preferably performed to obtain higher resolution alloy and thickness images (these need not necessarily be at the full resolution of the source image):

1. After upsampling the scatter estimate, it is downsampled to the required final resolution of the alloy and thickness images (if lower).
2. $I_C$ (the corrected image) is created at this intermediate resolution.
3. The non-implausible sets of alloy and thickness values are identified by comparing $I_C$ to a direct beam database at this resolution (as described later in relation to the generation of an updated model during the main refinement loop).
4. These sets are refined to a single estimate at each pixel using a spatial model.
5. The alloy and thickness estimates are then output at this resolution The thickness image 712, alloy image 714 and scatter corrected image 718 together form the main outputs 720 of the algorithm. These may be further processed as needed and/or output to an operator (for example, the thickness/alloy images could be used to generate colour coded scatter corrected images showing tissue density distributions or other visualizations useful to an operator).

Initial Estimate of the Tissue Model

The initial tissue model estimate—i.e. the initial set of thickness and alloy values—is determined based on a prior classification of image pixels likely to correspond to 100% soft tissue (i.e. an alloy value of 1), since these are generally easier to detect than intermediate alloy values. Embodiments may use thresholding of pixel intensity values in the recorded image to identify the regions of the image that are assumed to correspond to 100% soft tissue (on the assumption that very bright regions are likely to be 100% soft tissue). Machine vision techniques such as edge detection or neural networks may additionally be used.

Detection may also use stored data defining predetermined ranges ("non-implausible sets") of alloy and thickness values that could give rise to the recorded intensity at each pixel.

In one approach, the system can detect the thickness at particular points (i.e. x,y coordinates in the image plane), to give a constrained initial model of thicknesses. The system then uses the thickness values to infer alloy values.

Specifically, the prior 100% soft tissue classified regions are used as training data combined with the non-implausible sets obtained from comparing the image to a direct beam database (as described below). A non-implausible set is a set of all possible inputs which could give rise to what is observed, given applicable uncertainties. For example, a direct beam pixel intensity of some particular value might plausibly be caused by a range of specific tissue distributions. E.g. an intensity of 50 could hypothetically be caused by 10 cm of 100% soft tissue, 9 cm of 95% soft tissue and 5% bone, 8 cm of 90% soft tissue and 10% bone, or 1 cm of 55% soft tissue and 45% bone (note that these numbers are chosen purely for illustrative purposes and real values may differ), if only the direct beam is considered and there is zero uncertainty. If there is slight uncertainty about the observed intensity values (e.g. measurement error), and/or some uncertainty due to errors in interpolation or randomness of the simulator, then these sets could grow slightly e.g. by around +/−1 cm for a given alloy composition.

For prior-classified 100% soft tissue regions, the non-implausible sets are narrowed down by removing all thickness-alloy pairs which are not close to 100% soft tissue, producing a smaller collection of possible thicknesses which the algorithm then averages over. These thickness values are used as training points to fit a surface (referred to as a spatial model) which predicts thickness from (x,y) coordinates. This then provides an estimate of thickness for pixels which were not 100% soft tissue. For those pixels, the non-implausible sets are again narrowed down by removing all thickness-alloy pairs which are not close to the thickness estimate given by the derived surface, producing a smaller collection of possible alloy values for which an average is computed to yield the final alloy estimate.

The above process thus refines the thickness-alloy non-implausible sets to a single pair of thickness/alloy values at each coordinate, which are used as the tissue model for the initial iteration of the iterative refinement loop 204.

On subsequent iterations of the process, the same process can be repeated based on the scatter-corrected image instead of the original image (corrected using the scatter estimate determined in the current iteration) to produce a new tissue model as is discussed below.

The process is illustrated in FIG. 8A in generalised form. Specifically, FIG. 8A illustrates the creation of a tissue model for a current iteration n of the iterative refinement process. As described above for the creation of the initial issue model estimate, a spatial model 802 is obtained by constraining non-implausible sets of alloy and thickness values based on a priori classification of 100% soft tissue regions, averaging remaining plausible thickness values for 100% soft tissue pixels and fitting a thickness function to the image indicating an estimate of thickness at each pixel. From this, the tissue model comprising alloy and thickness images u 804 and t 806 are derived as previously described.

Iterative Refinement of the Tissue Model

FIG. 8B illustrates the refinement loop 204 of FIG. 2 in greater detail in one embodiment. The process starts in step 840 with the initial estimate of the tissue model, i.e. the initial set of alloy and thickness values, $\lambda_0$, $t_0$. The closer to the actual answer the initial estimate is, the quicker the algorithm should converge. The initial estimate of the tissue model is derived as described above and thus $\mu_0$ will contain information based on the prior-classified 100% soft tissue pixels ($\mu=1$), with non-100% soft tissue pixels having best guess thickness and alloy values.

The main loop then begins using the initial estimates $\lambda_2$, $\mu_0$ as the current values $\mu$, t on the first iteration.

At step 842, the current $\mu$, t is added to a stack of $\mu$, t estimates. Thus on the first iteration, $\mu_0$, $t_0$ become the first entry of the stack.

In step 844, the simulated scatter image (S) and direct beam image (D) are computed by the simulator for the current estimates $\mu$, t (this involves applying the transfer function to translate the simulation output into the real x-ray image domain). The scatter corrected real image ($I_C$) is then computed as the difference between the real source image I and the scatter estimate S. Additionally an error image ($I_E$) is computed by generating the full simulated image as the sum of the direct beam estimate D and scatter estimate S, and subtracting this from the real source image I. This error image therefore indicates the difference between the simulation output and the real image. The processing results of this step (scatter estimate S, direct beam estimate D, and corresponding corrected image $I_C$ and error image $I_E$) are collectively labelled (A) to distinguish from the alternative computation detailed below.

In step 846, a convergence test is performed to determine how close $I_E$ is to a zero image (i.e. an image having zero intensity at each pixel). The closeness may be computed as a single value error measure summarising the simulation error across the image, e.g. by summing over the individual pixel intensity values in $I_E$, which represent pixel differences between real and simulated image, to obtain a signed test statistic which is negative if the error image is predominantly negative (or positive if the image is predominantly positive). Note that alternative approaches may be used to determine the error measure. Convergence may then be determined by comparing the magnitude of the test statistic (error measure) to a threshold indicating when sufficient convergence has been achieved (though other suitable convergence criteria may be used). If the convergence criterion is met then the algorithm has converged and the iterative refinement process ends, with the system proceeding to perform post processing and produce the required outputs as described previously.

If convergence has not been achieved then the refinement loop continues. In step 848, the system compares $I_C$ to a precalculated database of direct beam (D) images and obtains non-implausible sets of μ, t at each pixel. The database of direct beam images is a stack of images of samples where for each image, the sample material corresponds entirely to a single thickness and alloy pair and thus each image shows how the intensity of the associated direct beam varies across the detector. Recall that this is not the same value at every pixel because each pixel has its own transfer function. This database is generated by computing simulated output for a direct beam over different thickness and alloy combinations and then applying the transfer function to each pixel of the resulting images.

In step 850, the prior-classified 100% soft tissue regions 852 are used to narrow down thickness estimates t for those pixels to those thicknesses which correspond to μ=100%. The prior classified soft tissue regions 852 are those originally identified based on pixel classification of the input image (though in other embodiments the classification could be updated at each iteration of the algorithm). This produces a small set of possible thickness values, and the system computes an average of the possible thickness values to obtain a thickness estimate at these 100% soft tissue pixels. The system then fits a thickness surface using the 100% soft tissue pixels as training points. This provides an estimate of thickness at all pixels and is referred to the spatial model. The system then narrows down the alloy values u of non-100% soft tissue pixels by constraining on the new thickness obtained from the derived thickness surface of the spatial model. This results in constraining the μ, t values sets at every pixel down to a single μ, t pair, thus yielding an updated tissue model μ, t for the whole image. The process of steps 848-850 thus mirrors the creation of the initial tissue model, but applied to the current scatter-corrected image $I_C$.

In step 854, the process computes S, D, $I_C$ and $I_E$ for this updated set of μ, t estimates, in the same manner as already described for step 844. This alternative result set is labelled (B) to distinguish it from the result set (A) produced by step 844.

At this stage, there are therefore two error images $I_E$ produced by this iteration, one produced using just the μ, t from the stack as computed at 844, label (A), and one that used the output of the spatial model as computed at 850, label (B).

The results of the alternative computations are compared at step 856, by determining which of $I_E$ (A) and $I_E$ (B) is closer to the convergence threshold (in terms of the derived error measure). If the new result $I_E$ (B) is better (lower magnitude error measure, meaning the error measure is closer to zero or closer to the threshold), in step 858 the process selects the μ, t determined at step 850 (B) as the new current μ, t values for the next iteration, and the process continues from step 842. Note on subsequent iterations of the loop, calculation time in step 844 can be saved since S, D, $I_C$ and $I_E$ have already been computed at step 854 and do not need to be computed again.

If, on the other hand, step 856 determines that $I_E$ (A), the original error image, is better (has a lower magnitude error measure), then the μ, t values from the spatial model calculation in step 850 (B) gave worse results. Nevertheless, in order to improve the materials information represented by the tissue model in some way, the system then averages the μ, t estimates of alloy and thickness from (B) with the best previous estimate (from previous iterations), which should be expected to lower the convergence test statistic (error measure). Specifically, the algorithm then averages the μ, t values from the output of the spatial model computation 850 with the μ, t entry from the stack which has the lowest error measure of the opposite sign (compared to the sign of the corresponding error measure for (B)) in step 860. This produces a refined tissue model μ, t for the next iteration, and the process continues as before at step 842 by adding the newly generated, averaged μ, t values as a new entry to the stack. However, in this case, the computations at step 844 cannot be skipped, since results for these newly derived μ, t values are not already available.

The stack thus tracks past μ, t estimates, and the best past estimates are used to correct the spatial model based estimates (B) when these fail to improve the simulation results. The process iterates in the above manner until convergence is reached in step 846 (e.g. until the absolute value of the error measure falls below the convergence threshold).

Note, in the above description, μ, t generally designate arrays of alloy and thickness values for the whole image (in other words, μ, t correspond to alloy and thickness images), though depending on context these terms may also refer to individual pixel μ, t values.

Computer System

FIG. 9 illustrates an example computer system, e.g. in the form of an image processing server 900, that may be used to implement the described algorithms. The server 900 comprises one or more processor(s) 902, a volatile memory (RAM) 904 for storage of software and data during software execution, and a network interface 906 for communication with other devices (e.g. detector 106, user interface device 114 and external storage 116 as depicted in FIG. 1).

The server further comprises persistent storage 908 (e.g. in the form of a magnetic storage medium such as a hard disk drive, FLASH memory or the like) for persistently storing software and data, which may include inter alia a calibration software process 910 for performing the calibration process described above, a scatter correction process 912 for performing the scatter correction process described above, and a simulator 916 for simulating X-ray interactions with material samples. The persistent storage may further comprise the direct beam and scatter kernel database 914 comprising pre-calculated direct beam and scatter kernel data computed by the simulator and used during the scatter correction process 912 to generate simulated image data for a given tissue model.

The server will typically contain other conventional hardware and/or software components as will be understood by one skilled in the art (e.g. a server operating system, I/O interfaces etc.)

The described system relies on the determination of materials information in order to predict and correct scatter. As such the final converged solution produces both a scatter-corrected X-ray image and a map of material composition and thickness (as the tissue model comprising the alloy image u and the thickness image t), the tissue model typically being at a lower resolution than the source X-ray image. Empirical evaluation has shown the composition and thickness returned by the algorithm to be within a few percent of the true values. The material composition (alloy)/thickness data can be used to compute and output relevant diagnostic indicators such as bone mineral density (BMD). For example, the BMD can be calculated as $(1-\mu)*t$ (e.g. this may be computed on a pixel basis and then optionally averaged over an image region of interest or over the entire image). The tissue model can also be used to provide visualisations e.g. through colour-coding the scatter-corrected image to indicate density distributions.

The described system can be used with any digital radiography detector and can provide some or all of the following benefits when compared to an anti-scatter grid:

Improved image quality without the artefacts associated with an anti-scatter grid.

Increased signal to noise ratio across the entire image for the same patient dose.

Optionally, reduced patient dose for the same image quality. It has been estimated that doses might be reducible by half or more whilst retaining the same image quality.

The system can provide body composition information which can be used to better discriminate tissue types or to calculate quantitative measures such as bone-mass density.

It will be understood that the present invention has been described above purely by way of example, and modification of detail can be made within the scope of the invention.

The invention claimed is:

1. A method of performing scatter correction on an X-ray image, comprising:
    obtaining an input image for processing based on a source X-ray image of a sample acquired using an X-ray detector;
    determining a model of the sample based on the input image, wherein the model comprises, for each of a plurality of locations, each location corresponding to at least one pixel of the input image, a thickness value indicating a thickness of the sample at the location and a material value indicative of a material composition of the sample at the location;
    evaluating the model by a process comprising:
        computing, based on the model, simulated X-ray image data;
        evaluating the simulated image data against the input image to determine whether a convergence criterion is fulfilled; and
        generating an updated model of the sample with updated thickness and material values if the convergence criterion is not fulfilled;
    the method comprising repeating the model evaluating process based on one or more successive updated models to iteratively refine the thickness and material values of the model until the convergence criterion is fulfilled in a final iteration; and
    performing at least one of:
        performing scatter correction on the source X-ray image using simulated image data computed during the final iteration; and
        outputting composition information for the sample based on the model of the sample used to generate the simulated image data determined to meet the convergence criterion during the final iteration.

2. A method according to claim 1, wherein the sample is modelled as consisting of first and second material types, the material value indicating material composition in relation to the first and second material types, preferably by indicating a proportion of one of the first and second material types at the location.

3. A method according to claim 1, wherein the simulated image data comprises:
    a direct beam image indicating an estimated contribution to the input image from X-ray photons passing through the sample without being scattered, and
    a scatter image indicating an estimated contribution to the input image from X-ray photons scattered by the sample.

4. A method according to claim 1, wherein computing simulated image data comprises computing simulated direct beam image data at each image location of the input image based on material composition and thickness values specified for the location in the model, and computing simulated scatter image data at each image location based on material composition and thickness values specified in the model for a plurality of other image locations.

5. A method according to claim 1, wherein computing simulated image data comprises determining a plurality of scatter kernels, each preferably specifying a scatter contribution due to the sample material at a first location to image pixels at one or more further locations, and generating a scatter image based on combining the plurality of scatter kernels, wherein the scatter kernels are optionally derived from a scatter kernel database based on the model, preferably by retrieving one or more precomputed scatter kernels and/or interpolating precomputed scatter kernels, the method optionally comprising modifying scatter kernels according to the material composition specified by the model for volume elements along scattered ray paths.

6. A method according to claim 1, wherein scatter correction is performed based on a scatter image of the simulated image data, preferably by subtracting an image correction determined based on the scatter image from the source X-ray image, optionally wherein the input image is obtained by downscaling the source X-ray image, the image correction determined by upscaling the scatter image to the resolution of the source X-ray image.

7. A method according to claim 1, wherein evaluating the simulated image data against the input image comprises applying a transfer function to one of the simulated image data and the input image and performing the evaluation after application of the transfer function, preferably wherein the transfer function defines a translation between simulated X-ray data and X-ray data obtained using the detector to make simulated X-ray data comparable to X-ray data obtained using the detector.

8. A method according to claim 7, wherein the transfer function defines a respective translation for each pixel location of the input image and simulated X-ray data, for translating intensity values between simulated and real image domains, the translation optionally in the form of a polynomial function, preferably of at least second degree, or other mathematical function.

9. A method according to claim 7, wherein the transfer function is empirically determined, preferably based on analysing a set of X-ray images acquired for predetermined known material samples and a set of corresponding simulated images generated for the known samples by the simulator.

10. A method according to claim 1, wherein evaluating the simulated image data against the input image comprises:
computing an error image based on the simulated image data and the input image, optionally by subtracting the scatter image and the direct beam image from the input image, wherein the error image comprises a plurality of error values for respective pixels based on the subtracting;
computing an error measure based on the error image, the error measure preferably indicating a degree of divergence of the error image from a zero image; and
comparing the error measure to a threshold, the convergence criterion preferably based on the threshold, the method comprising determining that the convergence criterion is met if the error measure falls below the threshold.

11. A method according to claim 1, wherein determining a model of the sample based on the input image comprises analysing the input image to classify one or more pixels as corresponding to a known material composition, preferably based on pixel intensity and/or feature detection, and determining the model using the classified pixels, optionally wherein the known material composition corresponds to the sample consisting of a single material at the pixel location.

12. A method according to claim 1, wherein generating an updated model of the sample comprises performing scatter correction on the input image based on the simulated image data, and generating the updated model based on the scatter-corrected input image.

13. A method according to claim 1, comprising performing a model generation process for an image comprising:
obtaining a classification of one or more pixels of the image as corresponding to a given material composition, the classification optionally based on comparison of intensity value(s) of the pixels to a threshold;
determining an estimated material thickness value for each of the one or more classified pixels, optionally based on data defining expected thickness values for pixels having the given material composition;
fitting a thickness function to the image based on estimated thickness values for the classified pixels, the thickness function indicating an estimated material thickness for each pixel of the image;
estimating material composition values for each pixel based on the estimated material thickness values specified by the thickness function, optionally by determining for each pixel a set of non-implausible material composition values based on the material thickness value for the pixel and deriving the material composition value for the pixel from the set of non-implausible material values, optionally by averaging the set of non-implausible material values; and
determining a model comprising for each pixel a material composition value and a thickness value based on the estimated material composition values and the estimated material thickness values.

14. A method according to claim 13, comprising performing the step of determining a model of the sample based on the input image by applying the model generation process to the input image.

15. A method according to claim 13, comprising performing the step of generating an updated model of the sample by computing a scatter-corrected version of the input image using the simulated image data (preferably by removing a simulated scatter image from the input image), and applying the model generation process to the scatter-corrected input image.

16. A method according to claim 1, comprising, after generating the updated model of the sample, computing new simulated image data based on the updated model and evaluating the new simulated image data against the simulated image data computed based on the model, and performing one of:
selecting the updated model for use in the subsequent iteration of the model evaluation process if the new simulated image data represents a simulated X-ray image closer to the input image than the simulated image data; and
if the simulated image data represents a simulated X-ray image closer to the input image than the new simulated image data, computing a revised updated model based on the updated model and a selected model determined in a previous iteration, and selecting the revised updated model for use in the subsequent iteration, preferably wherein the selected previous model is a model producing a lowest magnitude error measure of opposite sign when evaluating simulated image data against the input image.

17. A method according to claim 1, comprising outputting one or more of:
the scatter-corrected source X-ray image;
model data, preferably thickness and/or material composition data, for the sample, preferably based on the model of the sample used to generate the simulated image data determined to meet the convergence criterion during the final iteration.

18. A method according to claim 1, wherein the sample comprises biological tissue and/or wherein the model comprises a tissue model, optionally wherein the tissue model defines the sample as a plurality of thickness values and a plurality of composition values for respective volume elements in the tissue sample, preferably wherein the composition values specify a material composition for a volume element as a relative or fractional amount of one of two predetermined material types in the volume element, and wherein the predetermined material types are optionally soft tissue and bone.

19. A system comprising a processor with associated memory configured to perform operations including:
obtaining an input image for processing based on a source X-ray image of a sample acquired using an X-ray detector;
determining a model of the sample based on the input image, wherein the model comprises, for each of a plurality of locations, each location corresponding to at least one pixel of the input image, a thickness value indicating a thickness of the sample at the location and a material value indicative of a material composition of the sample at the location;
evaluating the model by a process comprising:
computing, based on the model, simulated X-ray image data;

evaluating the simulated image data against the input image to determine whether a convergence criterion is fulfilled; and generating an updated model of the sample with updated thickness and material values if the convergence criterion is not fulfilled;

the operations further including:

repeating the model evaluating process based on one or more successive updated models to iteratively refine the thickness and material values of the model until the convergence criterion is fulfilled in a final iteration; and performing at least one of:
  performing scatter correction on the source X-ray image using simulated image data computed during the final iteration; and
  outputting composition information for the sample based on the model of the sample used to generate the simulated image data determined to meet the convergence criterion during the final iteration.

20. A non-transitory computer-readable medium comprising software code which when executed is arranged to perform a method for scatter correction of an X-ray image, comprising:

obtaining an input image for processing based on a source X-ray image of a sample acquired using an X-ray detector;

determining a model of the sample based on the input image, wherein the model comprises, for each of a plurality of locations, each location corresponding to at least one pixel of the input image, a thickness value indicating a thickness of the sample at the location and a material value indicative of a material composition of the sample at the location;

evaluating the model by a process comprising:
  computing, based on the model, simulated X-ray image data;
  evaluating the simulated image data against the input image to determine whether a convergence criterion is fulfilled; and
  generating an updated model of the sample with updated thickness and material values if the convergence criterion is not fulfilled;

the method comprising repeating the model evaluating process based on one or more successive updated models to iteratively refine the thickness and material values of the model until the convergence criterion is fulfilled in a final iteration; and performing at least one of:
  performing scatter correction on the source X-ray image using simulated image data computed during the final iteration; and
  outputting composition information for the sample based on the model of the sample used to generate the simulated image data determined to meet the convergence criterion during the final iteration.

* * * * *